US012156818B2

(12) United States Patent
Aghayev et al.

(10) Patent No.: US 12,156,818 B2
(45) Date of Patent: Dec. 3, 2024

(54) EXPANDABLE INTER VERTEBRAL CAGE

(71) Applicants: H. LEE MOFFITT CANCER CENTER AND RESEARCH INSTITUTE, INC., Tampa, FL (US); University of South Florida, Tampa, FL (US)

(72) Inventors: Kamran Aghayev, Tampa, FL (US); James J. Doulgeris, Oldsmar, FL (US); Sabrina A. Gonzalez Blohm, Tampa, FL (US); Frank D. Vrionis, Tampa, FL (US)

(73) Assignees: H. Lee Moffitt Cancer Center and Research Institute, Inc., Tampa, FL (US); University of South Florida, Tampa, FL (US)

(*) Notice: Subject to any disclaimer, the term of this patent is extended or adjusted under 35 U.S.C. 154(b) by 248 days.

(21) Appl. No.: 17/669,994

(22) Filed: Feb. 11, 2022

(65) Prior Publication Data

US 2022/0304820 A1 Sep. 29, 2022

Related U.S. Application Data

(63) Continuation of application No. 16/443,302, filed on Jun. 17, 2019, now Pat. No. 11,246,717, which is a (Continued)

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/30168* (2013.01); *A61F 2002/30171* (2013.01); *A61F 2002/30261* (2013.01); *A61F 2002/30383* (2013.01); *A61F 2002/30398* (2013.01); *A61F 2002/30405* (2013.01); *A61F 2002/305* (2013.01); *A61F 2002/30525* (2013.01); *A61F 2002/30545* (2013.01); *A61F 2002/3055* (2013.01); *A61F 2002/30556* (2013.01); *A61F 2002/30565* (2013.01); *A61F 2002/30571* (2013.01);

(Continued)

(58) Field of Classification Search
CPC .................... A61F 2/447; A61F 2/4455; A61F 2002/30836
See application file for complete search history.

(56) References Cited

U.S. PATENT DOCUMENTS

| | | | |
|---|---|---|---|
| 4,456,005 | A | 6/1984 | Lichty |
| 4,858,601 | A | 8/1989 | Glisson |

(Continued)

FOREIGN PATENT DOCUMENTS

| | | |
|---|---|---|
| WO | 2013/052807 | 4/2013 |

OTHER PUBLICATIONS

International Preliminary Report on Patentability and Written Opinion, dated Jun. 21, 2016, received in connection with International Patent Application No. PCT/US2014/070899.

(Continued)

*Primary Examiner* — Nicholas J Plionis
(74) *Attorney, Agent, or Firm* — Perkins Coie LLP

(57) ABSTRACT

A method and system for performing bone fusion and/or securing one or more bones, such as adjacent vertebra, are disclosed.

24 Claims, 33 Drawing Sheets

120a
140
140
120b
150

Related U.S. Application Data continuation of application No. 15/500,969, filed as application No. PCT/US2015/043109 on Jul. 31, 2015, now Pat. No. 10,322,009.

(60) Provisional application No. 62/031,955, filed on Aug. 1, 2014.

(52) U.S. Cl.
CPC ............... *A61F 2002/30579* (2013.01); *A61F 2002/30836* (2013.01); *A61F 2002/30904* (2013.01)

(56) References Cited

U.S. PATENT DOCUMENTS 5,171,278 A 12/1992 Pisharodi
5,609,635 A 3/1997 Michelson
6,039,761 A 3/2000 Li et al.
6,517,543 B1 2/2003 Berrevoets et al.
6,821,298 B1 11/2004 Jackson
6,921,403 B2 7/2005 Cragg
7,217,293 B2 5/2007 Branch, Jr.
7,799,057 B2 9/2010 Hudgins et al.
7,879,098 B1 2/2011 Simmons, Jr.
8,043,334 B2 10/2011 Fisher et al.
9,351,848 B2 5/2016 Glerum et al.
9,482,260 B1 11/2016 Krause
9,566,168 B2 2/2017 Glerum et al.
9,820,788 B2 11/2017 Vrionis et al.
10,105,238 B2 10/2018 Koch et al.
10,314,631 B2 6/2019 Vrionis et al.
10,322,009 B2 6/2019 Aghayev et al.
10,390,963 B2 8/2019 Olmos
10,500,059 B2 12/2019 Grotz
10,687,876 B2 6/2020 Vrionis et al.
10,792,083 B2 10/2020 Vrionis et al.
10,799,367 B2 10/2020 Vrionis et al.
2002/0195827 A1 12/2002 Jackson et al.
2004/0122431 A1 6/2004 Biedermann et al.
2004/0210227 A1 10/2004 Trail et al.
2005/0043735 A1 2/2005 Ahmad
2005/0070911 A1 3/2005 Carrison et al.
2005/0113917 A1 5/2005 Chae et al.
2005/0143735 A1 6/2005 Kyle
2005/0197660 A1 9/2005 Haid et al.
2005/0261683 A1 11/2005 Veldhuizen et al.
2005/0261695 A1 11/2005 Cragg et al.
2005/0277923 A1 12/2005 Sweeney
2006/0036322 A1 2/2006 Reiley
2006/0224241 A1 10/2006 Butler et al.
2006/0287725 A1 12/2006 Miller
2007/0167951 A1 7/2007 Ainsworth et al.
2007/0270855 A1 11/2007 Partin
2008/0183204 A1 7/2008 Greenhalgh et al.
2009/0076607 A1 3/2009 Aalsma et al.
2009/0118771 A1 5/2009 Gonzalez-hernandez
2009/0254129 A1 10/2009 Tipirneni et al.
2009/0281628 A1 11/2009 Oglaza et al.
2010/0003638 A1 1/2010 Collins et al.
2010/0036440 A1 2/2010 Morris et al.
2010/0049244 A1 2/2010 Cohen et al.
2010/0082109 A1* 4/2010 Greenhalgh ............ A61F 2/447 623/17.15
2010/0285783 A1 11/2010 Huguet et al.
2011/0034925 A1 2/2011 Tipirneni et al.
2011/0035011 A1 2/2011 Cain
2011/0087294 A1 4/2011 Reiley
2011/0144703 A1 6/2011 Krause et al.
2011/0224738 A1 9/2011 Sucec et al.
2011/0301712 A1 12/2011 Palmatier
2011/0319946 A1 12/2011 Levy et al.
2012/0123546 A1 5/2012 Medina
2012/0209386 A1 8/2012 Triplett
2013/0006361 A1* 1/2013 Glerum ................ A61F 2/4455 623/17.16
2013/0053902 A1 2/2013 Trudeau
2013/0103156 A1 4/2013 Packer
2013/0190876 A1 7/2013 Drochner
2013/0190877 A1 7/2013 Medina
2013/0211526 A1* 8/2013 Alheidt .................. A61F 2/442 623/17.16
2013/0231747 A1 9/2013 Olmos et al.
2013/0325075 A1 12/2013 Jackson
2013/0325128 A1 12/2013 Perloff et al.
2014/0012383 A1 1/2014 Triplett et al.
2014/0052253 A1 2/2014 Perloff
2014/0094916 A1 4/2014 Glerum et al.
2014/0114312 A1 4/2014 Krause et al.
2014/0277139 A1 9/2014 Vrionis et al.
2014/0277490 A1 9/2014 Perloff
2015/0012048 A1 1/2015 Huebner et al.
2015/0073552 A1* 3/2015 To ....................... A61B 17/025 623/17.15
2016/0310190 A1 10/2016 Gonzales et al.
2016/0338846 A1 11/2016 Walker
2017/0056200 A1 3/2017 Koch et al.
2018/0014866 A1 1/2018 Vrionis et al.
2018/0078384 A1 3/2018 Suddaby
2018/0092677 A1 4/2018 Peterson et al.
2018/0092751 A1 4/2018 Vrionis et al.
2018/0071000 A1 6/2018 Pham et al.
2018/0193164 A1 7/2018 Shoshtaev
2018/0250051 A1 9/2018 Vrionis et al.
2019/0046328 A1 2/2019 Rosenwasser et al.

OTHER PUBLICATIONS

International Search Report and Written Opinion, dated May 14, 2015, received in connection with International Patent Application No. PCT/US2014/070899.

International Preliminary Report on Patentability and Written Opinion, dated Apr. 8, 2014, received in connection with International Patent Application No. PCT/US2012/058968.

International Search Report and Written Opinion, dated Mar. 28, 2013, received in connection with International Patent Application No. PCT/US2012/058968.

International Search Report and Written Opinion in Application No. PCT/US15/43109, dated Nov. 2, 2015.

International Preliminary on Patentability issued in Application No. PCT/US15/43109, dated Feb. 16, 2017.

* cited by examiner

EXPANDABLE INTER VERTEBRAL CAGE

CROSS REFERENCE TO RELATED APPLICATIONS

This application is a continuation of U.S. application Ser. No. 16/443,302, filed Jun. 17, 2019. U.S. application Ser. No. 16/443,302 is a continuation of U.S. application Ser. No. 15/500,969, filed Feb. 1, 2017, titled "Expandable Intervertebral Cage" (now U.S. patent Ser. No. 10/322,009). U.S. application Ser. No. 15/500,969 is a national stage application filed under 35 U.S.C. § 371 of PCT/US2015/043109, filed Jul. 31, 2015, which claims the benefit of U.S. Provisional Application No. 62/031,955, filed Aug. 1, 2014. Each of the above-mentioned applications are incorporated herein by reference in their entireties.

TECHNICAL FIELD

This disclosure relates to neurosurgical and orthopedic fixation systems.

BACKGROUND

Spinal interbody fusion is a frequently performed procedure to treat various disorders such as degenerated disk disease, spondylolisthesis, trauma, infection, tumor and deformity. Usually, surgery involves placement of screws into the vertebral body through the vertebral pedicle and/or placement of an interbody cage with bone grafts into the disc space. Types of spinal fusion depend on the approach type such as posterior, transforaminal, lateral, etc. Although these approaches claim to be minimally invasive, they still require open incisions for cage and screw placement as well as compression and/or distraction of vertebral bodies. Improvements in the devices' design enhance spinal fusion as well as minimize the invasiveness of the surgical implantation, which are desirable traits in clinical practice.

SUMMARY

Presented are systems and methods for providing fusion and distraction between adjacent vertebral bodies. An aspect of the present disclosure is directed to an intervertebral cage including an upper bar and an opposing lower bar. The cage can further include a separator movable between the upper bar and the lower bar to cause movement of the upper bar towards and away from the lower bar. The cage can also include a pin having a first end extending into an opening provided in the upper bar and a second end extending into an opening provided in the second bar.

Another aspect of the present disclosure is directed to an intervertebral cage including a first upper bar and opposing first lower bar. The cage can also include a first and second separator movable between the first upper bar and the first lower bar to cause movement of the first upper bar towards and away from the first lower bar. The cage can further include a second upper bar and opposing second lower bar and a third and fourth separator movable between the second upper bar and the second lower bar to cause movement of the second upper bar towards and away from the second lower bar. The cage can also include a threaded rod, where each of the bars include an arm extending from a side surface of each of the corresponding bars, the arms engaging the threaded rod.

The details of one or more implementations of the invention are set forth in the accompanying drawings and the description below. Other features, objects, and advantages of the invention will be apparent from the description and drawings, and from the claims.

DESCRIPTION OF DRAWINGS

The device is explained in even greater detail in the following exemplary drawings. The drawings are merely exemplary to illustrate the structure of preferred devices and certain features that may be used singularly or in combination with other features. The invention should not be limited to the implementations shown.

DETAILED DESCRIPTION

Certain exemplary implementations of an expandable intervertebral cage used to facilitate fusion between two vertebral bodies will now be described with reference to the drawings.

The cage 100 is designed for implantation and fusion between two vertebrae. The cage 100 can be implanted, for example between adjacent cervical, thoracic, lumbar, or sacral vertebrae. In non-expanded state, the cage 100 can be inserted through a small incision into the disc space or between two adjacent bones. Once expanded, the cage 100 can be used to provide distraction between the adjacent vertebrae or bones. As will be described in more detail below, the cage 100 can expand horizontally and/or vertically. For example, once positioned as desired by a medical professional, the cage 100 can be expanded in a horizontal direction; for example, in the horizontal plane of the intervertebral space in which the cage 100 is located. The cage 100 can also be expanded in a vertical direction to increase the vertical separation between the adjacent vertebrae. The horizontal expansion can be performed before the vertical expansion. A single actuator, or plurality of actuating devices, can be used to provide horizontal and vertical expansion. In one example, an actuator(s) can be used to first cause horizontal expansion followed by vertical expansion. In this way, a low height and width profile of the unexpanded cage 100 can be used for implantation and then with use of an actuator, the width and height profile can be expanded as desired. The space between the deployed components of the cage 100 can be accessed for placement of a bone filling material.

Figure 1:
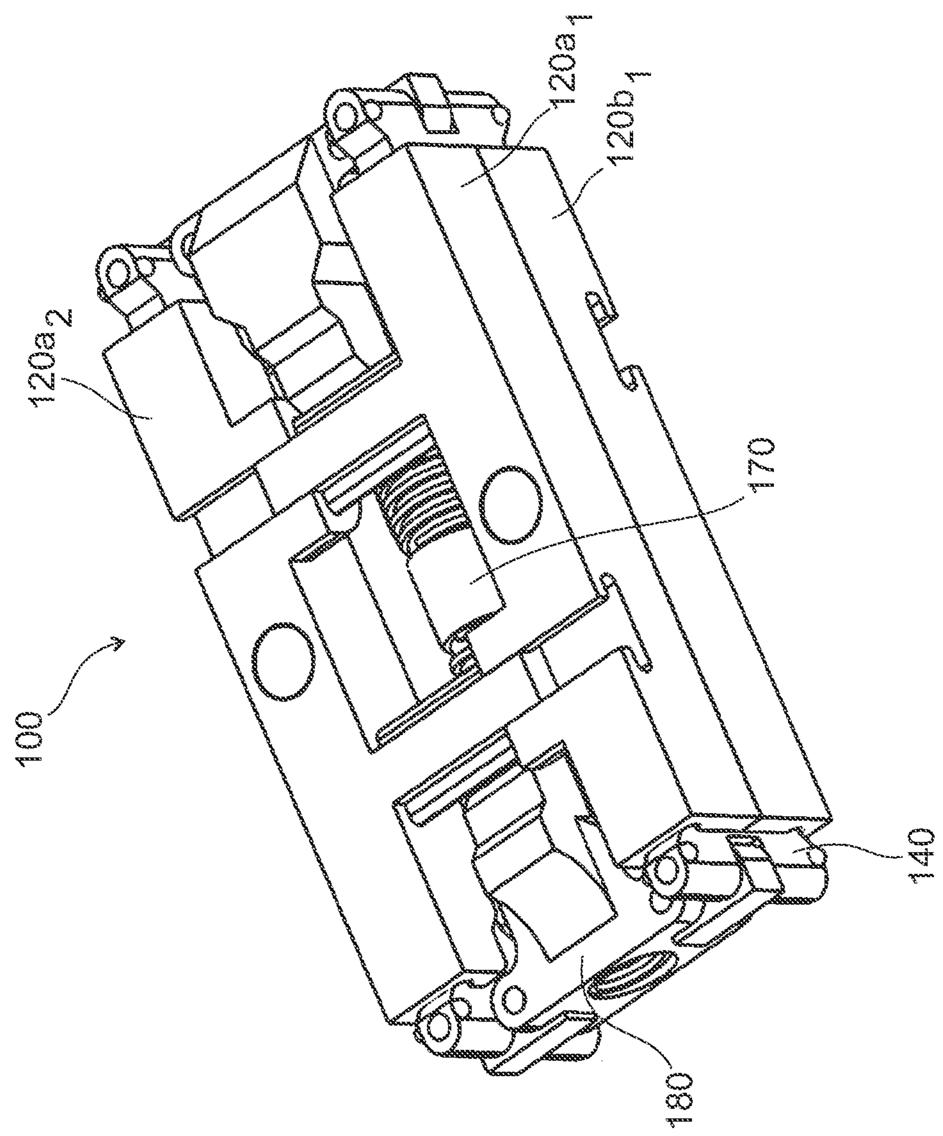
FIG. 1 is a perspective view if an example intervertebral cage.

FIG. 1 is a perspective view of an example intervertebral cage 100. The cage 100 can include two pairs of upper and opposing lower longitudinal bars 120, e.g., upper and lower bars 120$a_1$, 120$b_1$ and upper and lower bars 120$a_2$, 120$b_2$. Each pair includes an upper bar 120$a$ and a lower bar 120$b$ and the pairs are spaced from one another across the vertical midline of the cage 100. As will be described in more detail below, the lateral and vertical space between the bars 120 can be increased/decreased and the cage 100 is expanded/retracted (the cage 100 illustrated in FIG. 1 is expanded in only the lateral direction). A separator 140 can be used to provide define a distance/separation between the upper and lower bar pairs 120$a$, 120$b$ and the height of the cage 100 in an expanded configuration. As will be described below, a threaded rod 170 and spacer 180 can be used to control/limit lateral and vertical expansion between adjacent bar pairs 120$a_1$, 120$b_1$ and 120$a_2$, 120$b_2$.

Figure 2A:
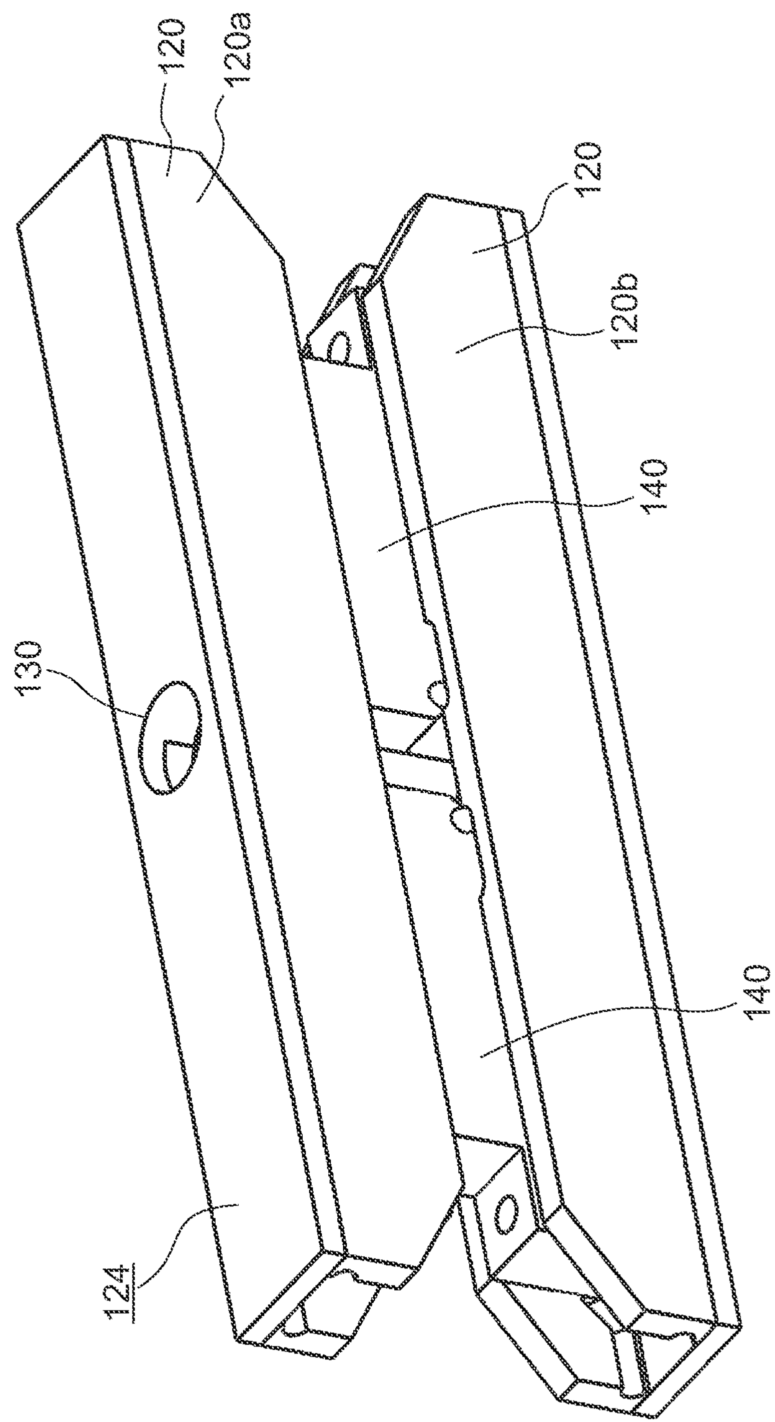
FIG. 2A is a perspective view of an example bar pair.
Figure 2B:
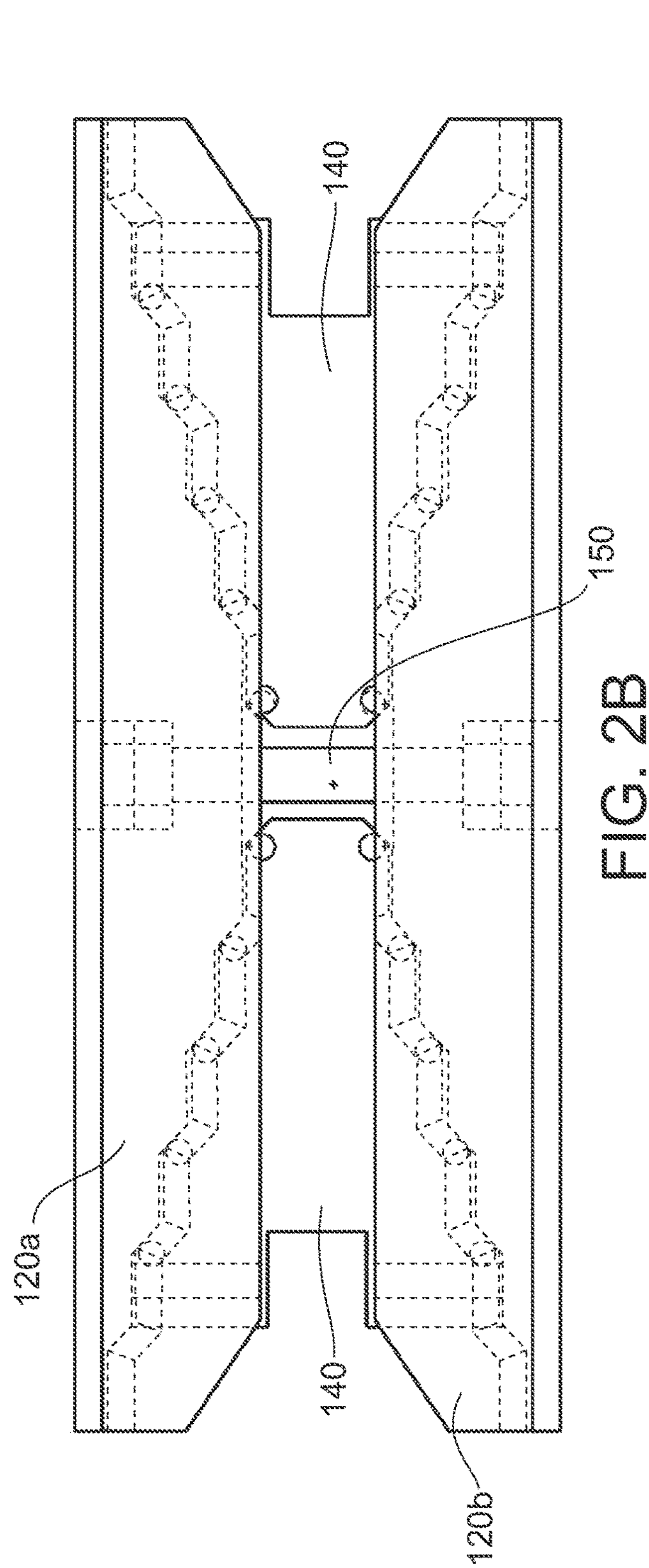
FIG. 2B is a front view of the example bar pair of FIG. 2A in an expanded configuration.
Figure 2C:
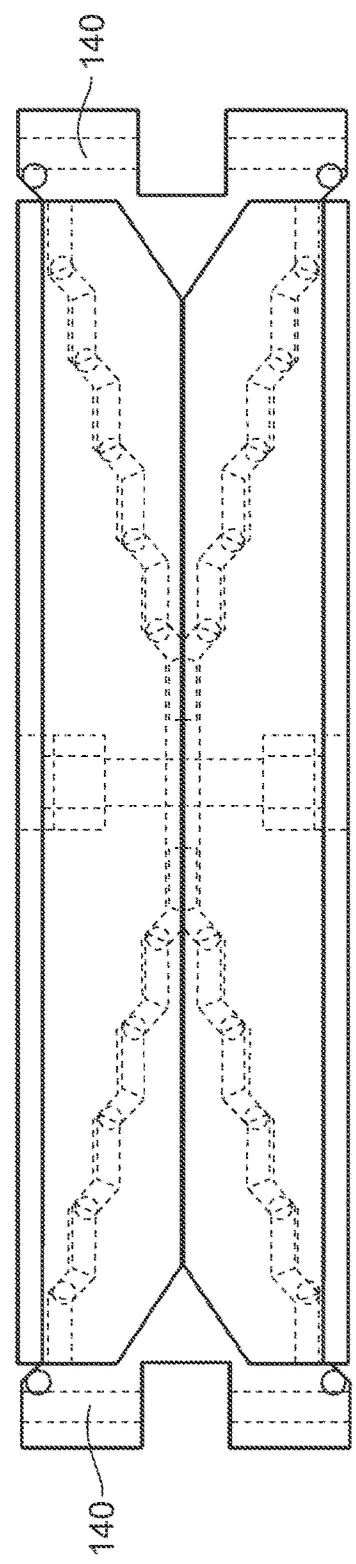
FIG. 2C is a front view of the bar pair of FIG. 2A in an unexpanded configuration.

FIG. 2A is a perspective view of an example bar pair including upper bar 120$a$ and lower bar 120$b$. FIG. 2B is a front view of the example bar pair 120$a$, 120$b$ of FIG. 1 in an expanded configuration. FIG. 2C is a front view of the example bar pair 120$a$, 120$b$ of FIG. 1 in an unexpanded configuration. As illustrated in FIGS. 2B and 2C, and as will be described in more detail below, the separator 140 can be movable between the upper bar 120$a$ and the lower bar 120$b$ to cause movement of the bars towards and away from each other.

Figure 3A:
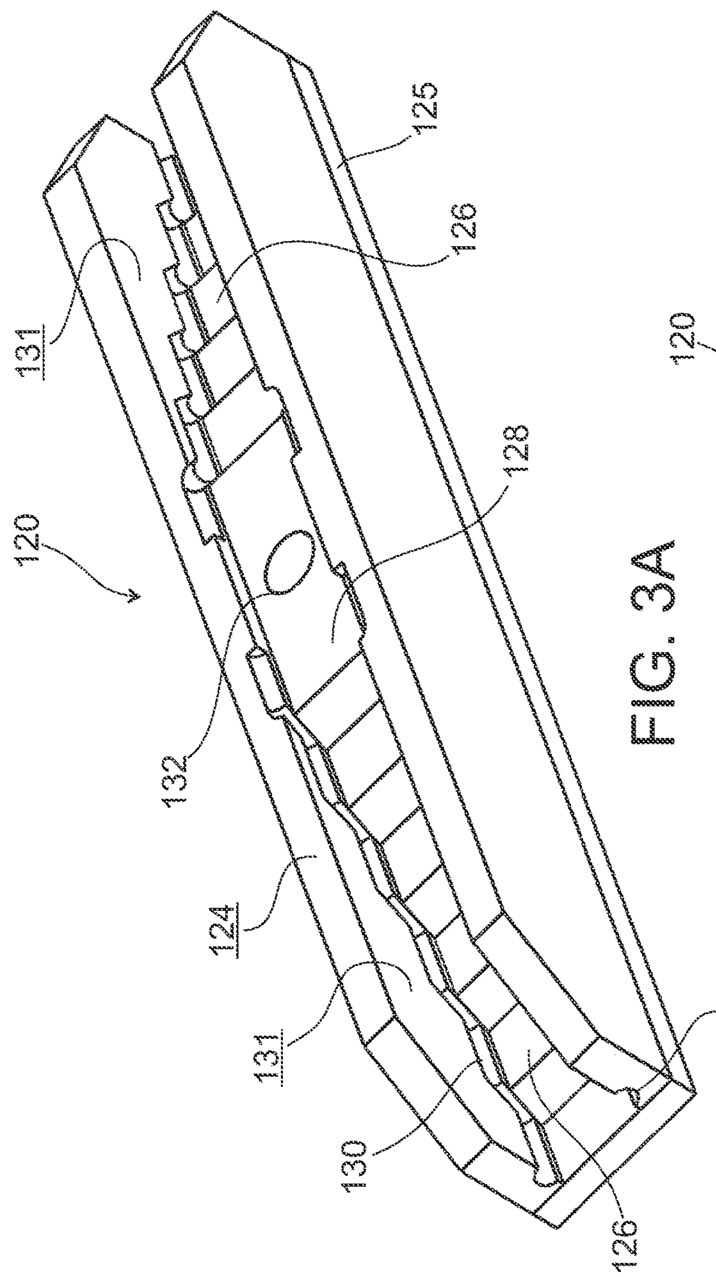
FIGS. 3A and 3B are perspective views of an example bar.
Figure 3B:
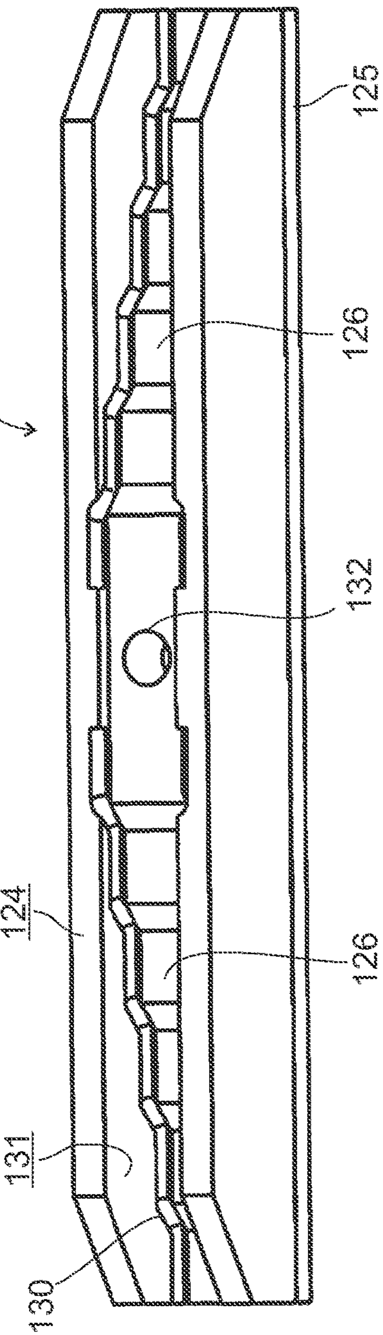
Figure 7:
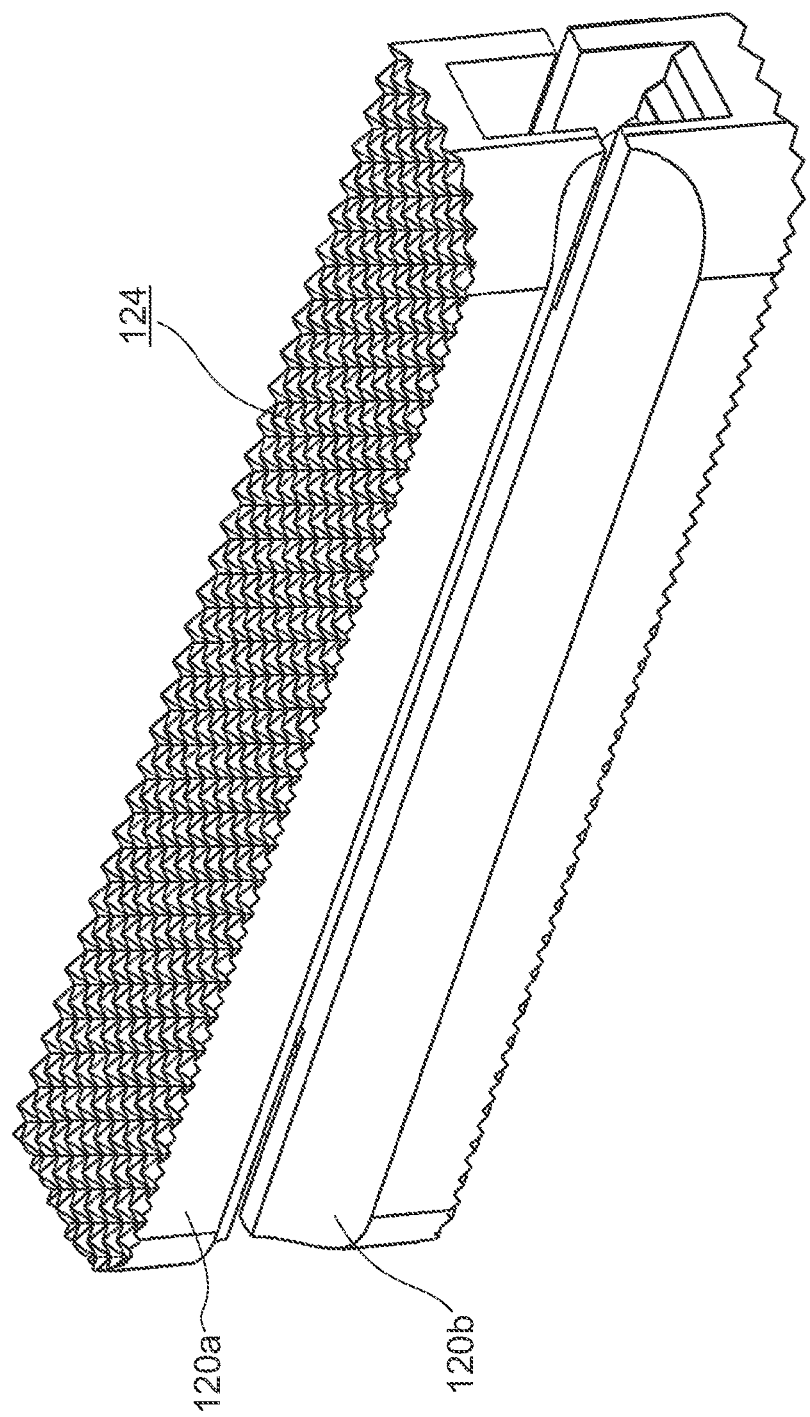
FIG. 7 is a perspective view of example upper and lower bar pair.

FIGS. 3A and 3B are perspective views of an example upper bar 120$a$ and/or lower bar 120$b$. The bar can include a top surface 124 and an opposing vertebral body contacting surface 125 for contacting the vertebral endplates of the adjacent vertebral bodies. The vertebral body contacting surface 125 can bend, deform or consist of specific surface area (either of irregular or regular shape) to accommodate the endplate of the adjacent vertebral body. The vertebral body contacting surface 125 can also consist of a sloping surface to intentionally induce uneven expansion. Likewise, the vertebral body contacting surface 125 of the upper and lower bars 120$a$, 120$b$ can include teeth or ridges for engaging the endplates of the adjacent vertebral bodies as shown, for example, in FIG. 7. The teeth can provide engagement and/or increased purchased between the cage 100 and the adjacent vertebral bodies. The teeth can have a pyramid shape (polygonal base and triangular faces that meet at a common point) or any other shape that can be used to provide increased friction, surface area contact and engagement between the bar 120 and the adjacent vertebral endplate. It is also contemplated that the vertebral body contacting surface 125 can include any type of biological or non-biological coating to enhance bone growth and attachment (fusion) with the cage 100.

As illustrated in FIGS. 3A and 3B, the bar 120 can also include a contact surface 126 for contacting a corresponding surface 142 provided on the separator 140 such that movement of the separator 140 along the bar's contact surface 126 can increase and/or decrease the spacing between the upper and lower bars 120$a$, 120$b$. Initially a lateral bar pair can be provided in the unexpanded configuration as illustrated in FIG. 2C. In the unexpanded configuration the separator 140 is provided on the contact surface 126 proximate the end of the bar 120. Movement of the separator 140 towards the midline of the bar 120 increases the spacing between the upper and lower bars 120$a$, 120$b$ and drives the cage 100 from an unexpanded to a vertically expanded configuration.

As illustrated in FIGS. 3A and 3B, the contact surface 126 can be inclined towards the midline of the bar 120 and configured to engage a corresponding inclined contact surface 142 of the separator 140. As illustrated in FIGS. 2B-2C and 3A-3C, contact surface 126 can include an inclined stepped surface. Likewise, the contact surface 142 of the separator 140 can include a corresponding inclined stepped surface. Because the upper and lower bars 120$a$ and 120$b$ are under compression when implanted, the flats of the stepped contact surface 126 prevent the separator 140 from backing out when under pressure. Likewise, the distance between adjacent flats can define the discrete expansion value for each step (e.g., 1 mm, 2 mm, 3 mm, 4 mm). It is contemplated that the contact surface 126 and/or the corresponding contact surface 142 can define a straight/flat surface, a curved surface (e.g., convex, concave, etc.) or any other regular or irregular shaped surface. While the distance between flats of a stepped design can define the expansion value of the separator 140, an inclined design can have continuous expansion values ranging between, for example, 1 mm-4 mm.

Though not illustrated, the upper and/or lower bars 120*a*, 120*b* can include a single contact surface 126. In another example, and as illustrated in FIGS. 3A and 3B, the bar 120 can include two contact surfaces 126 provided at opposite ends of the bar 120. The contact surfaces 126 can terminate at a stop surface 128 proximate the top surface 124 of the bar 120. In another example (not shown), the contact surfaces 142 can terminate at a common edge or intersection point, e.g., the intersection point of two separator contact surfaces provided on the bar 120.

Figure 3D:
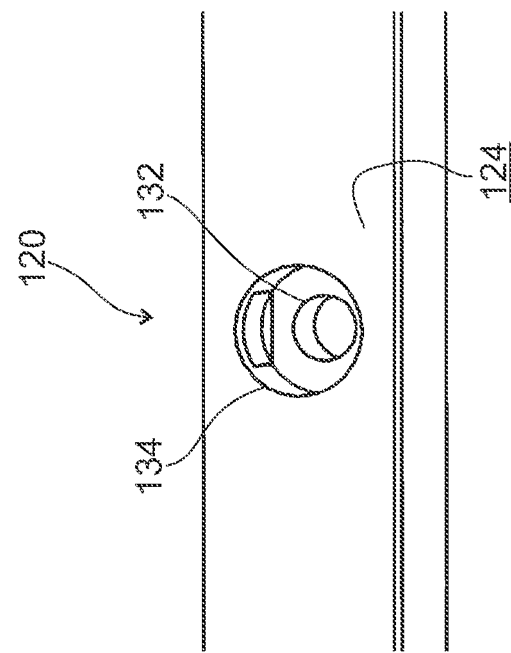
FIG. 3D is a partial top perspective view of an example bar.
Figure 3C:
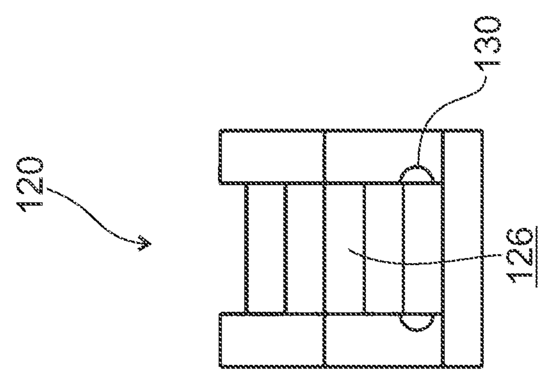
FIG. 3C is an end view of an example bar.

As provided in FIGS. 3A-3C, the bar 120 can include a groove 130 included on an inside surface 131 of the bar 120. The groove 130 can be inclined towards the midline of the bar 120 and configured to engage a corresponding projection 144 extending from a side surface 146 of the separator 140, illustrated in FIGS. 4A-4D. As illustrated in FIGS. 3A-3C, the groove 130 can be stepped and be provided proximate the contact surface 126. In another example (not shown), the groove 130 can be provided at any location on an inside surface 131 of the bar 120 separate from the location of the contact surface 126. In a further example (not shown), bar 120 does not include a contact surface 126 and the groove 130 can be provided on an inside surface 131 of the bar 120.

Figure 4B:
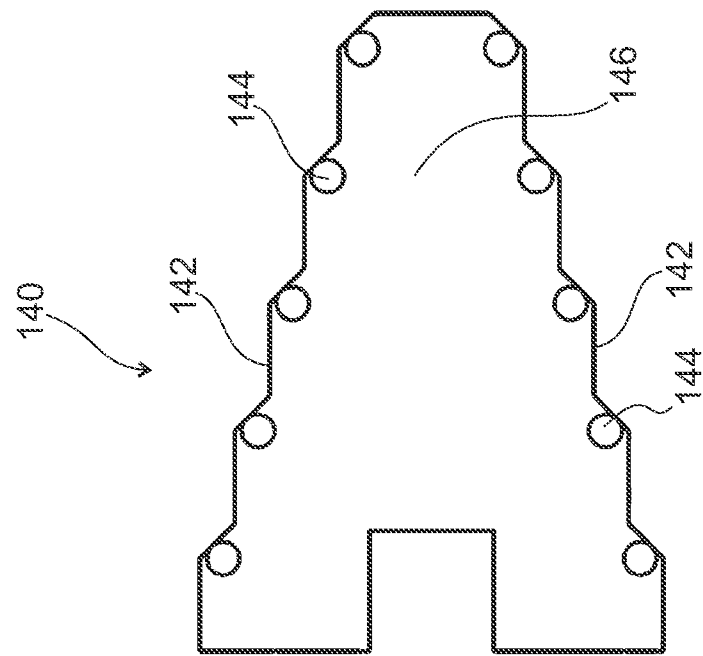
FIG. 4B is a side view of an example separator.
Figure 4A:
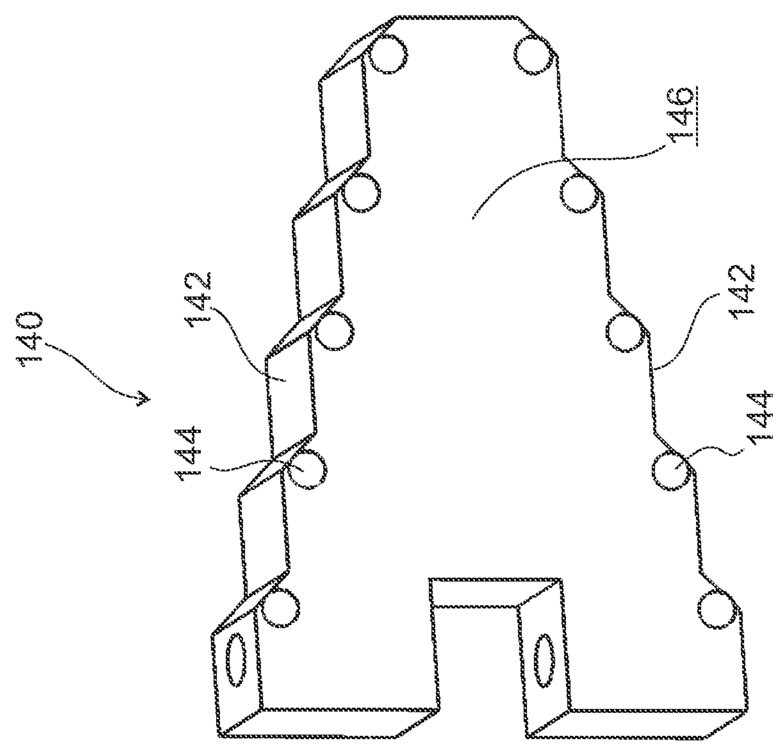
FIG. 4A is a perspective view of an example separator.
Figure 4D:
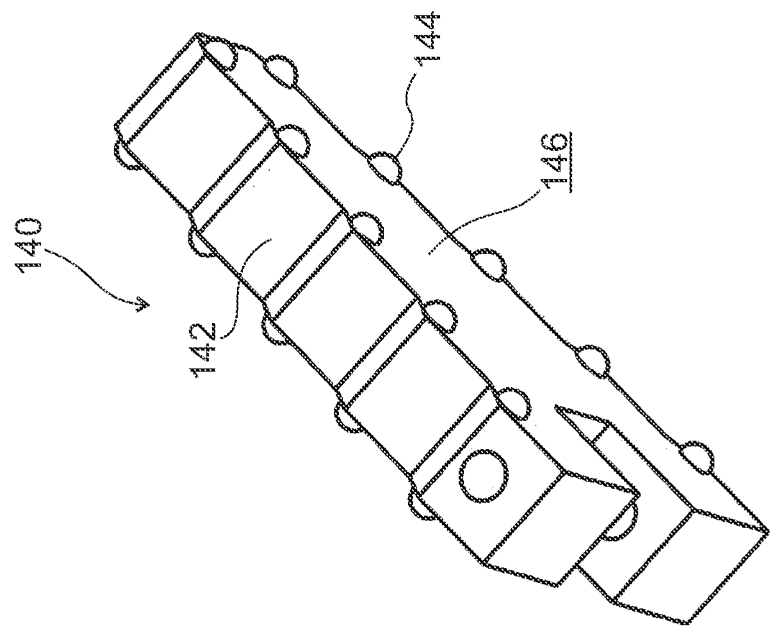
FIGS. 4C and 4D are perspective view of an example separator.
Figure 4C:
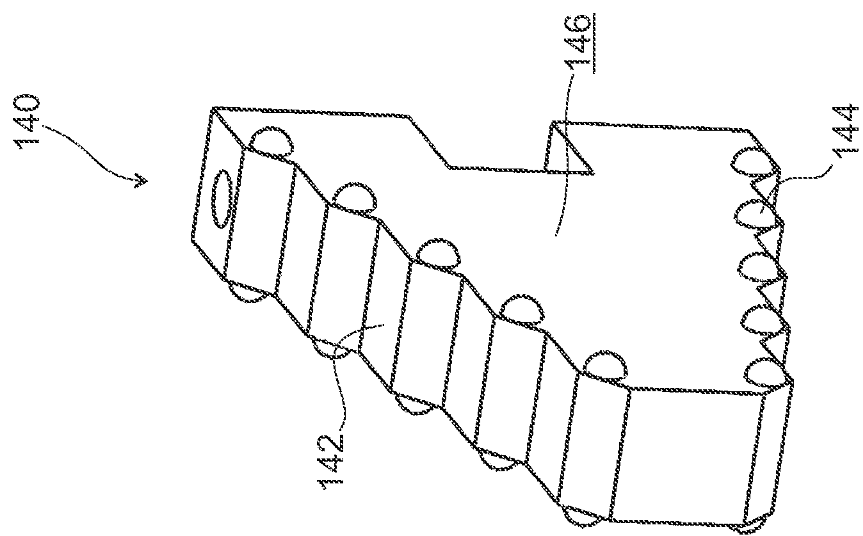
Figures 5A, 5B:
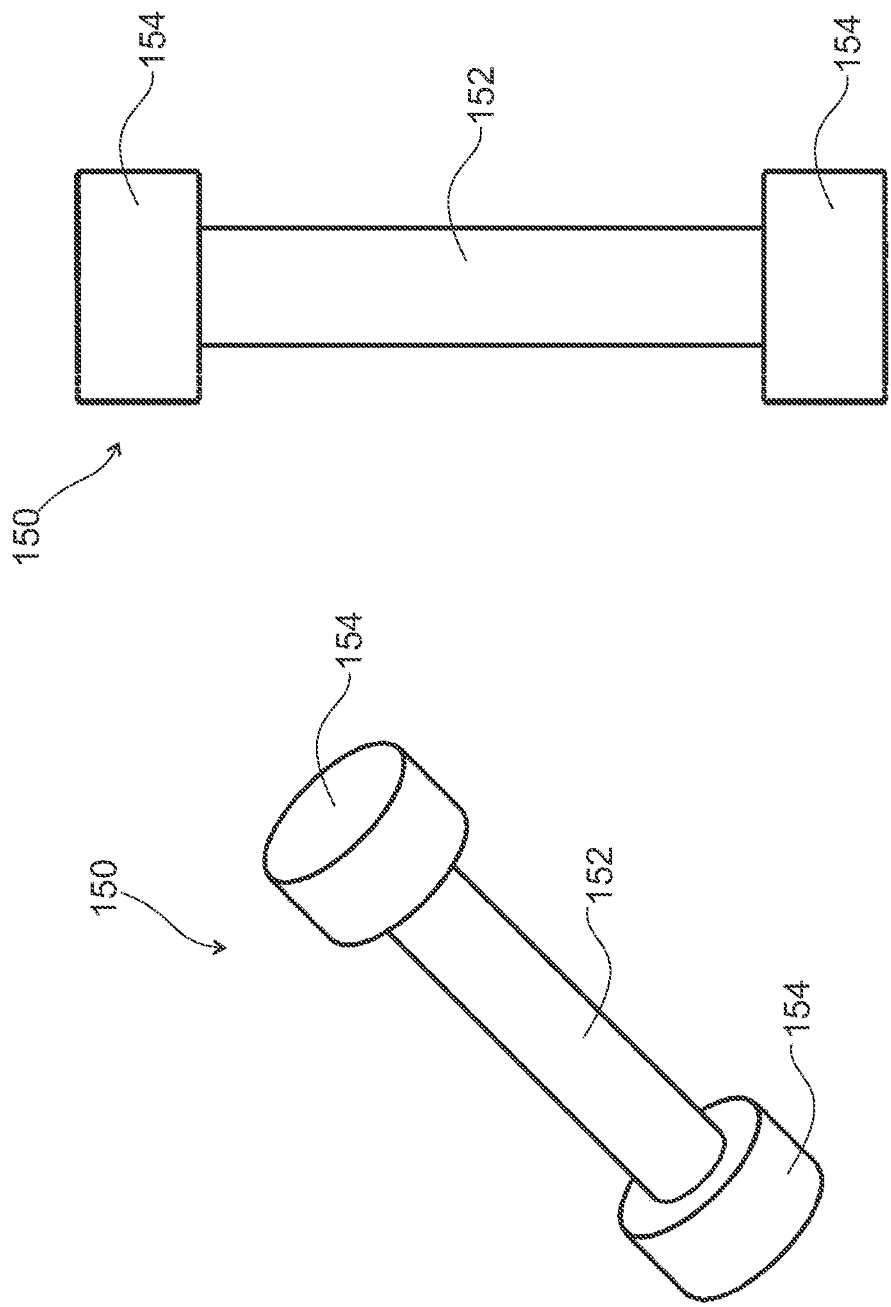
FIG. 5A is a perspective view of an example pin.
FIG. 5B is a front view of an example pin.
Figure 5D:
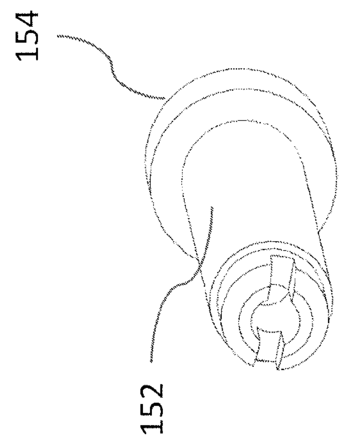
FIGS. 5C and 5D are perspective views of an example partial pin.
Figure 5E:
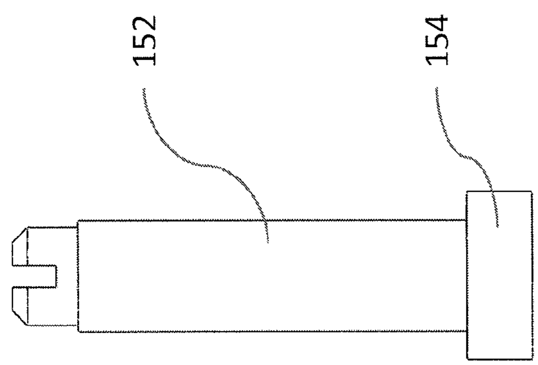
FIG. 5E is a front view of an example partial pin.
Figure 5C:
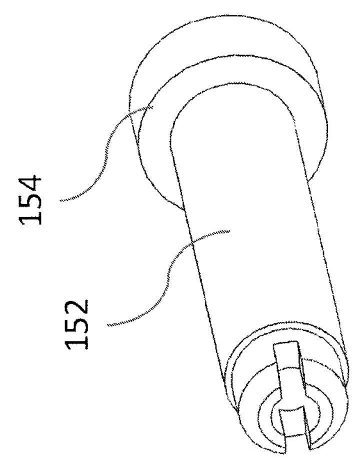
Figure 5G:
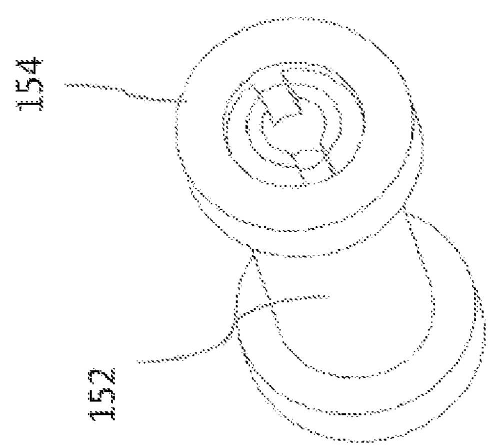
FIGS. 5F and 5G are perspective views of an example pin.
Figure 5F:
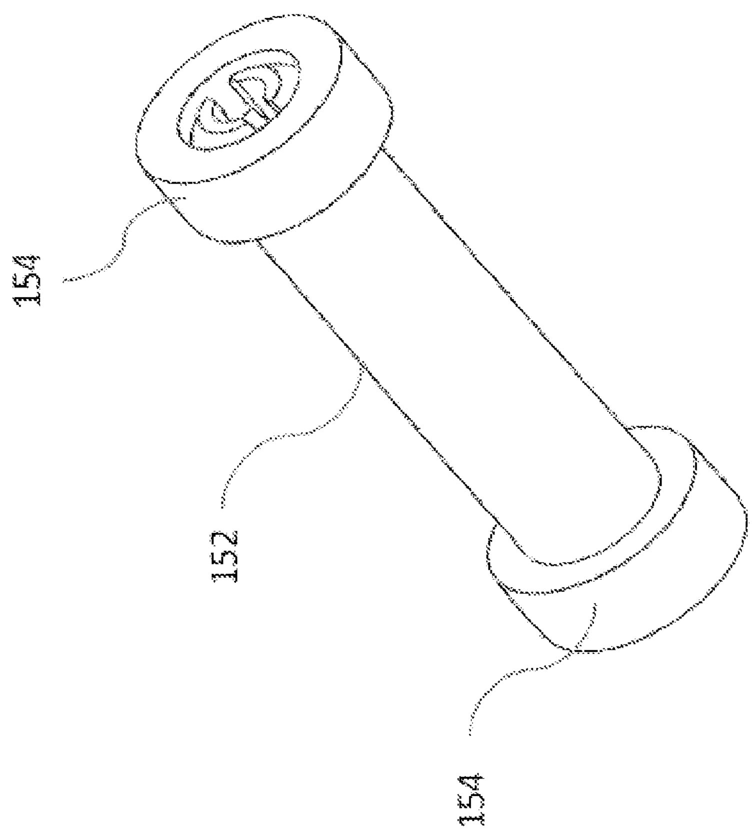

FIGS. 4A, 4C and 4D provide perspective views of an example separator 140. FIG. 4B is a side view of the example separator 140. As illustrated, the separator 140 can include an inclined and/or stepped contact surface 142. The projection 144 for engaging the groove 130 provided in the bar 120 can be located on the side of the separator 140 proximate the contact surface 142. The separator 140 can include a single projection 144 or a plurality of projections 144. The projections 144 can sized and shaped to slidably engage the groove 130. For example, the projection 144 can define a round/hemispherical shape, or any other regular or irregular shape that permits movement between the projection 144 and the groove 130. During use, engagement of the projection 144 and the groove 130 guides movement of the separator 140 with respect to the bar 120 from an unexpanded to expanded configuration, and vice versa. Engagement between the projection 144 and the groove 130 also helps to maintain contact and/or spacing between the contact surface 126 and the contact surface 142. FIGS. 5A and 5B provide a perspective and front view of an example pin 150. The pin 150 can include a main body 152 and a head 154. The main body 152 can include an elongated shaft extending between two head portions 154 where the heads 154 have a width/diameter greater than a width/diameter of the main body 152. The head 154 can be of a regular or an irregular shape and the pin 150 can consist of a symmetrical, as illustrated in FIG. 5A, or asymmetrical shape (not illustrated). The pin 150 extends through/into and is movable within an opening 132 in the bars 120. The pin 150 can be used to maintain alignment of the upper bar 120*a* and lower bar 120*b* during compression and distraction of the cage

100, i.e., movement between the unexpanded and expanded configuration. For example, the pin 150 can maintain the upper bar 120*a* and the lower bar 120*b* in a parallel configuration. The upper bar 120*a* and/or lower bar 120*b* can include a recessed opening 134 as illustrated in FIG. 3D showing a partial top perspective view of the top surface 124 of an example bar 120. The recessed opening 134 can have a width/diameter larger than the width/diameter of the main opening 132 and can be sized and configured to receive the head 154 of the pin 150. The depth of the recessed opening 134 can define the limits of expansion of the cage 100. That is, as the bottom of the heads 154 of the pin 150 impact/contact the bottom surface of the recessed opening 134 the cage 100 is prevented from further expansion. Accordingly, the distance between the heads 154 of the pin 150 can define the amount of expansion between the upper bar 120*a* and the lower bar 120*b*. Movement of the pin 150 within the openings 132 provided in the upper and lower bars 120*a*, 120*b* also prevents the bars 120 from shearing, that is, the pin 150 prevents the bars 120 moving from left to right with respect to each other. The pin 150, including the main body 152 and head(s) 154 can have unitary construction. In another example, illustrated in FIGS. 5C-5G, the main body 152 and head(s) 154 can be constructed from separate pieces coupled during assembly of the cage 100. For example, the main body 152 can be inserted through/into the main opening 132 of the upper and lower bars 120*a*, 120*b* and the heads 154 can be coupled (permanently and/or removably coupled) to the opposing ends of the main body 152. The main body 152 and head 154 can be coupled via press fit, snap fit, or any other form of mechanical fastening.

Figure 6A:
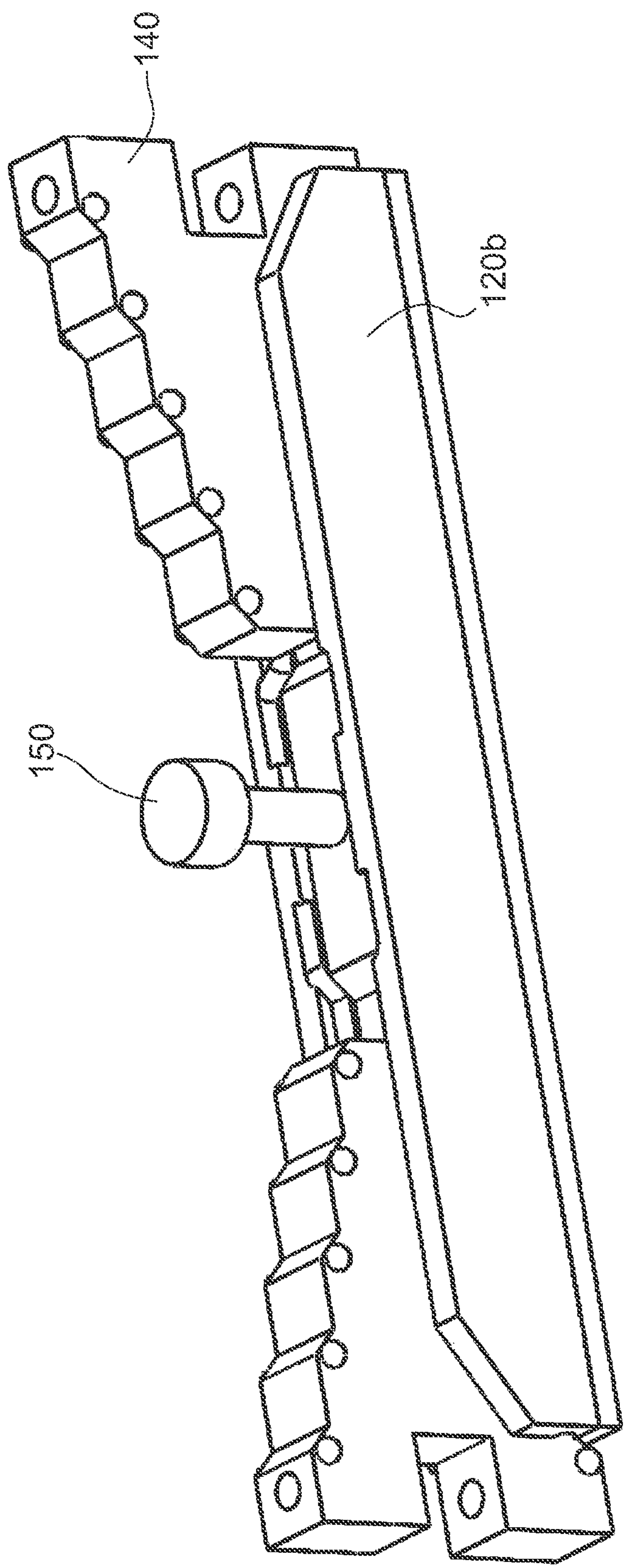
FIG. 6A is a perspective view of an example lower bar, separators, and pin.
Figure 6B:
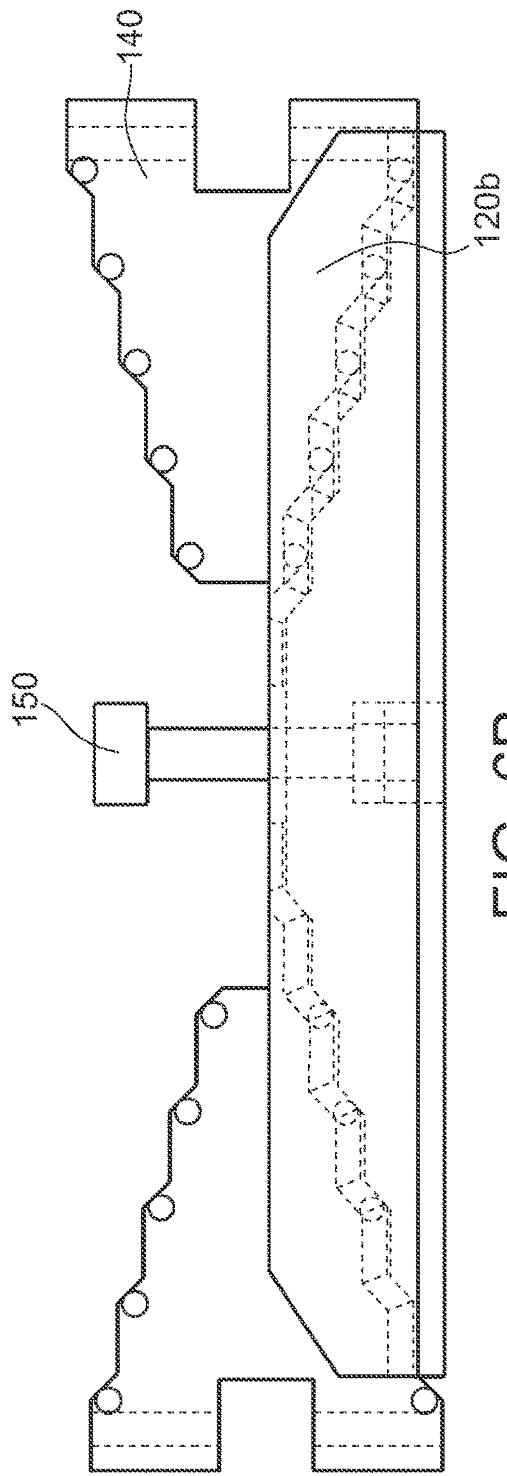
FIG. 6B is a front view of an example lower bar, separators, and pin in an unexpanded configuration.
Figure 6C:
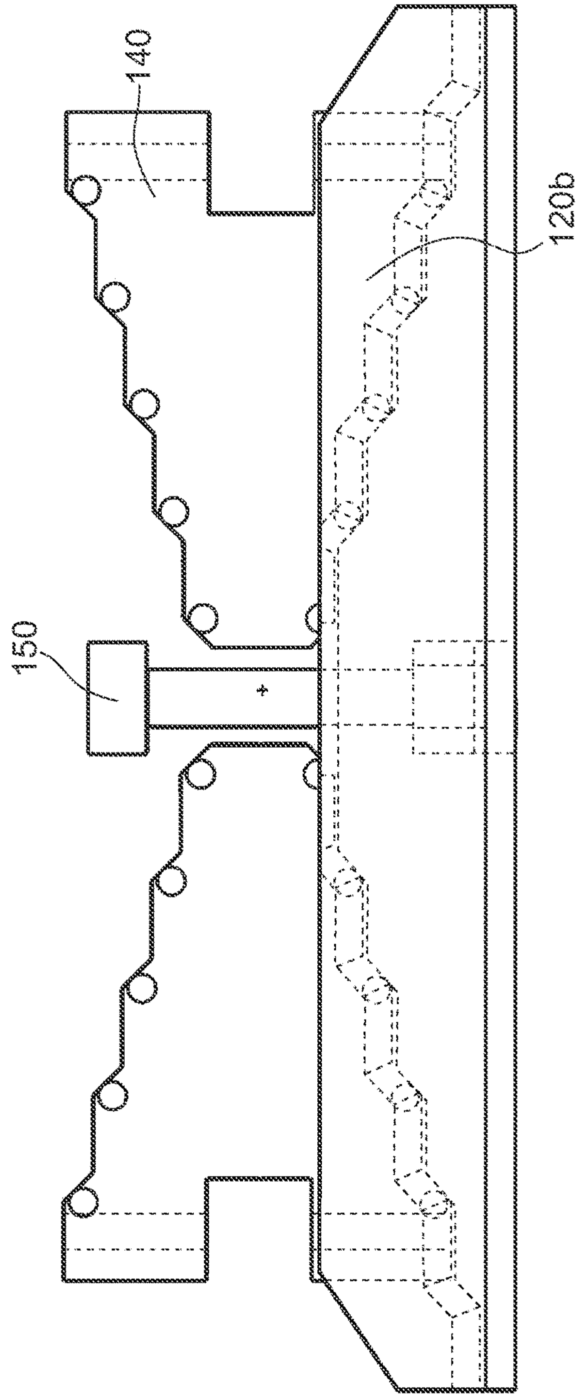
FIG. 6C is a front view of an example lower bar, separators, and pin in an expanded configuration.

FIGS. 6A-6C show an example front view of an assembled lower bar 120*b*, separator 140 and pin 150. FIGS. 6A and 6B illustrate the lower bar 120*b* and separators 140 in an unexpanded configuration and FIG. 6C illustrates the lower bars 120*b* and separators 140 in an expanded configuration.

Figure 8A:
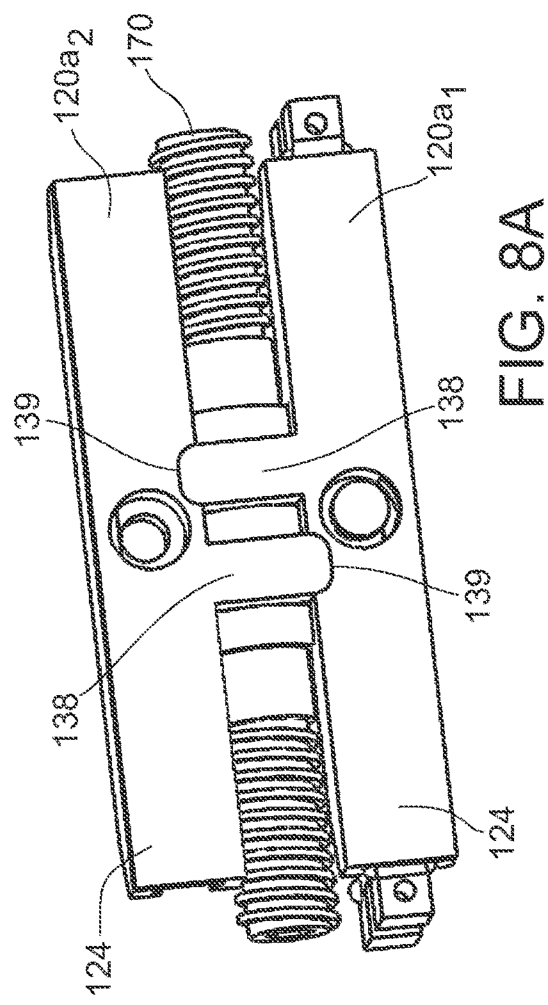
FIGS. 8A and 8B are top perspective views of opposing upper bars and threaded rod.
Figure 8B:
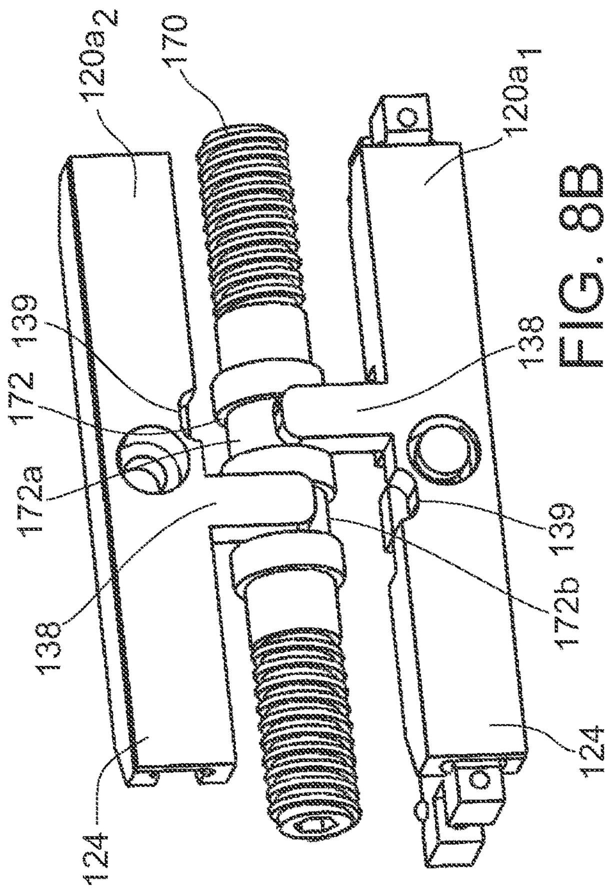
Figure 8C:
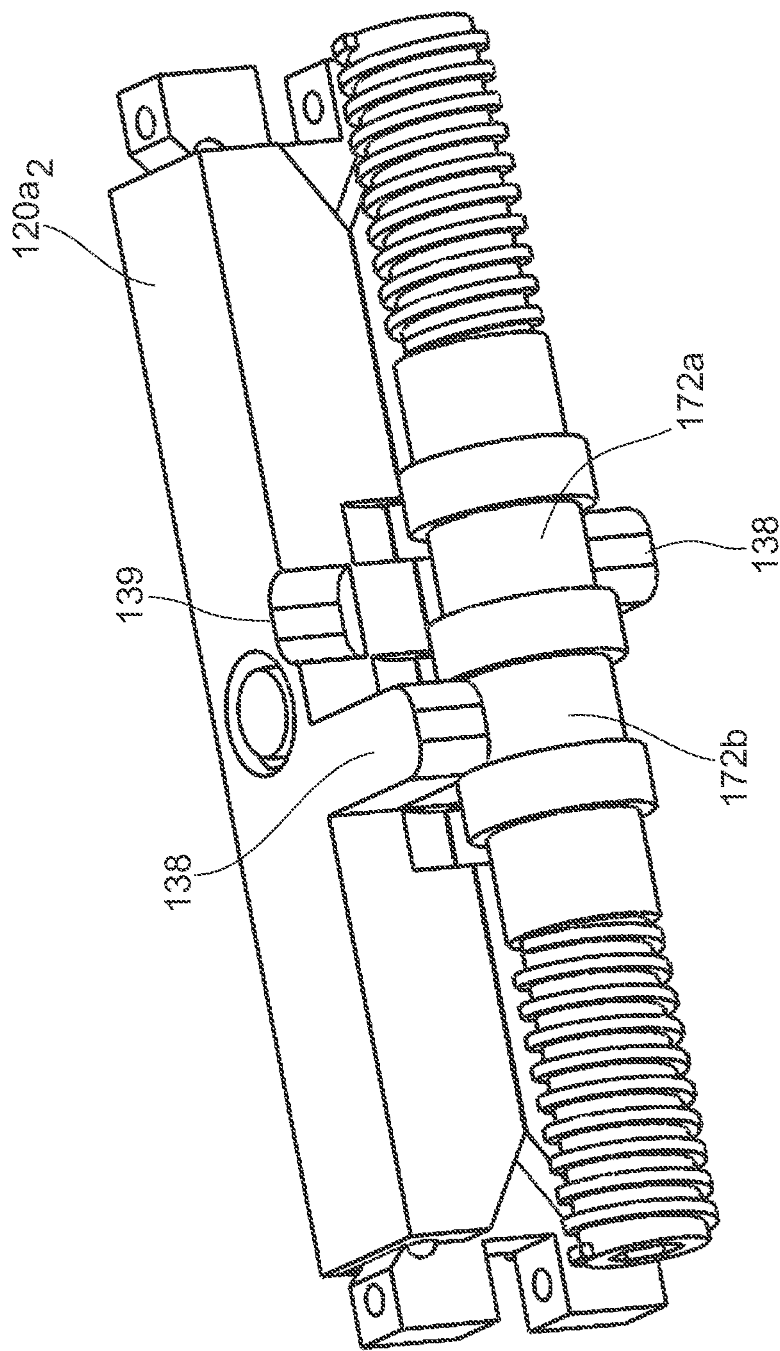
FIG. 8C is a perspective view of an example threaded rod and upper and lower bar pair.

As outlined above, a threaded rod 170 can be used for controlling/limiting lateral and vertical expansion between adjacent bar pairs $\mathbf{120}a_1$, $\mathbf{120}b_1$ and $\mathbf{120}a_2$, $\mathbf{120}b_2$. FIGS. 8A and 8B illustrate a top perspective view of example threaded rod 170 opposing upper bars $\mathbf{120}a_1$ and $\mathbf{120}b_1$. FIG. 8C is a perspective view of the example threaded rod 170 and upper and lower bar pair $\mathbf{120}a_2$ and $\mathbf{120}b_2$. While the example cage 100 includes two upper and a lower bar pairs $\mathbf{120}a_1$, $\mathbf{120}b_1$ and $\mathbf{120}a_2$, $\mathbf{120}b_2$, it is contemplated that cage 100 can also include a single pair of upper and lower bars 120*a*, 120*b* used in conjunction with a single actuator, or plurality of actuating devices, to provide horizontal and/or vertical expansion. For example, FIG. 8C illustrates an example of a cage 100 including a single pair of upper and lower bars 120*a*, 120*b* used in conjunction with a threaded rod.

FIGS. 8A and 8B show a top view of upper bars $\mathbf{120}a_1$ and $\mathbf{120}a_2$ in an unexpanded (FIG. 8A) and horizontally expanded (FIG. 8B) configuration. The space between opposing upper bars $\mathbf{120}a_1$, $\mathbf{120}a_2$ can be widened when the cage is expanded in the horizontal/lateral direction. Likewise, the space between opposing lower bars $\mathbf{120}b_1$ and $\mathbf{120}b_2$ can be widened when the cage is expanded in the horizontal/lateral direction. As provided in FIGS. 8A-8C, at least one of the bars 120 includes an arm 138 extending from a top surface 124 of the bar 120. For example, as illustrated in FIGS. 8A-8C, each bar 120 of the upper and lower bar pairs $\mathbf{120}a_1$, $\mathbf{120}b_1$ and $\mathbf{120}a_2$, $\mathbf{120}b_2$ include an arm 138 extending from a top surface 124 of the bar 120. The arm 138 extends in a direction towards the adjacent bar pair and engages the threaded rod 170. The threaded rod 170 can include a channel(s) 172 for engaging the arms 138 such that the arms 138 are movable (in a perpendicular direction) with respect to the threaded rod 170. For example, as the threaded rod 170 rotates, the arm 138 is maintained within the channel 172 and the shear movement between the opposing bars is limited. Shear movement of one bar pair (e.g., 120$a_2$, 120$b_2$) with respect to the opposite side bar pair (e.g., 120$a_1$, 120$b_1$) is controlled/limited by contact between the arm 138 and the side of the channel 172. As illustrated in FIGS. 8A-8C, the example threaded rod 170 can include two channels 172 (first channel 172$a$ and second channel 172$b$). To prevent interference, the arms 138 extending from the upper bars 120$a_1$, 120$a_2$ engage opposite channels, e.g., the arm 138 extending from the first upper 120$a_1$ bar can engage the first channel 172$a$ and the arm extending from the second upper bar 120$a_2$ can engage the second channel 172$b$. Likewise, the arms extending from the lower bars 120$b$ can engage different channels, e.g., the arm extending from the first lower bar 120$b_1$ can engage the second channel 172$b$ and the arm extending from the second lower bar 120$b_2$ can engage the first channel 172$a$. The upper and lower bars 120$a$, 120$b$ can also include a recess 139 for receiving all or a portion of the arm 138 extending from the opposing upper/lower bar 120$a$, 120$b$. For example, as illustrated in FIGS. 8A and 8B, the first upper bar 120$a_1$ can include a recess 139 for receiving a portion of the arm 138 extending from the second upper bar 120$a_2$. Likewise, the second upper bar 120$a_2$ can include a recess 139 for receiving a portion of the arm 138 extending from the first upper bar 120$a_1$. The recess 139 allows the intervertebral cage 100 to have a smaller size when in an unexpanded configuration by allowing the arms 138 to overlap with each of the opposing bars 120. In an example cage 100, the recess 139 can define the limit of lateral movement between opposing bar pairs 120$a_1$, 120$b_1$ and 120$a_2$, 120$b_2$ towards each other. The arms 138 and corresponding recesses 139 can be located at any point along the length of the bar 120. As illustrated in FIGS. 8A-8C, the arms 138 and recesses 139 are located proximate the pin 150 location. It is contemplated, however, that the arms 138 and recesses 139 can be located proximate the ends of the bars 120. The arms 138 and recesses 139 can also be located at positions symmetrical or asymmetrical about the midline plane of the bars 120.

Figure 9A:
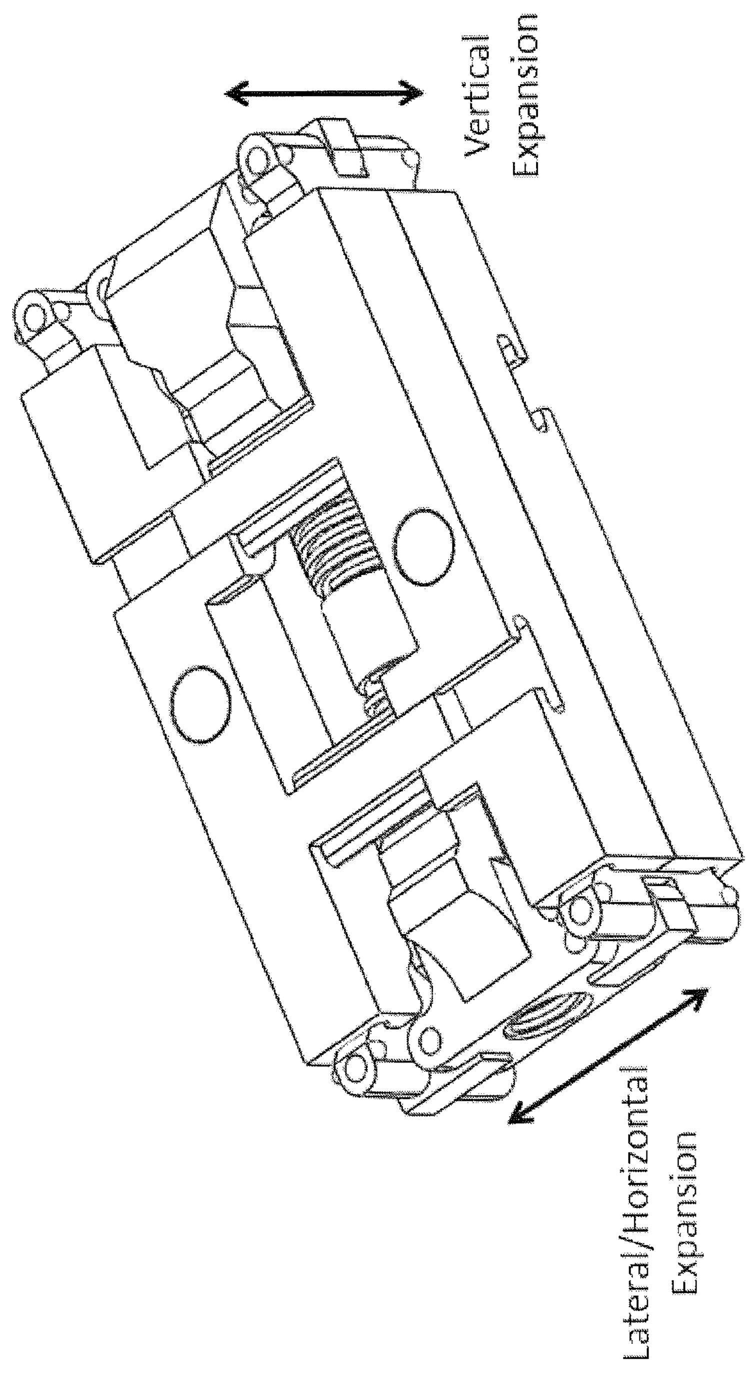
FIGS. 9A-9D are perspective views of an example intervertebral cage.
Figure 9B:
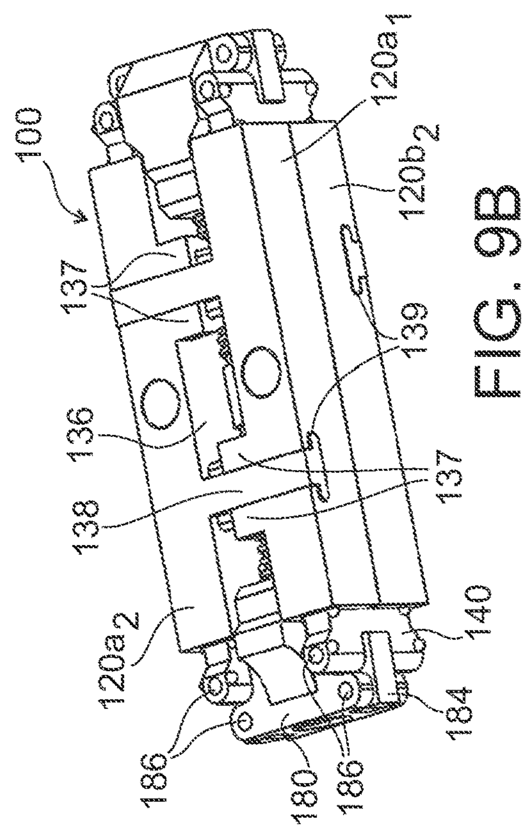
Figure 9D:
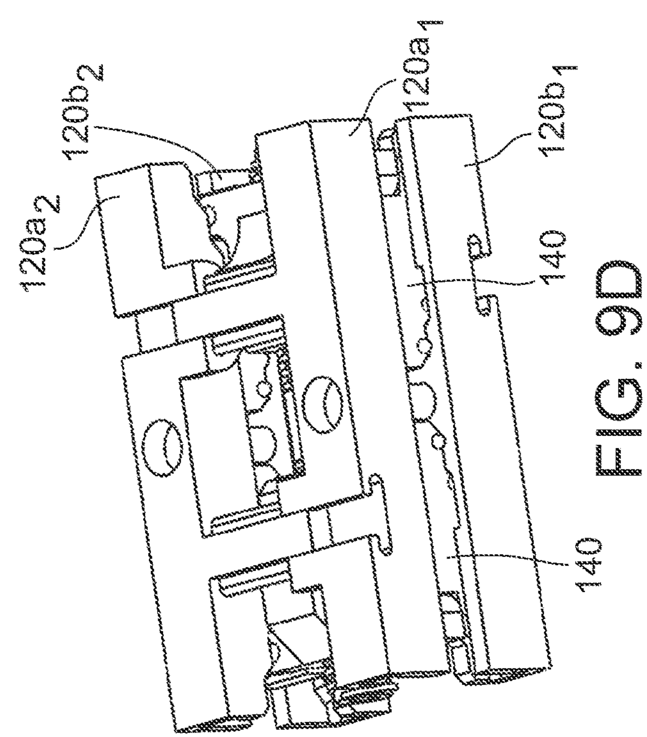
Figure 9C:
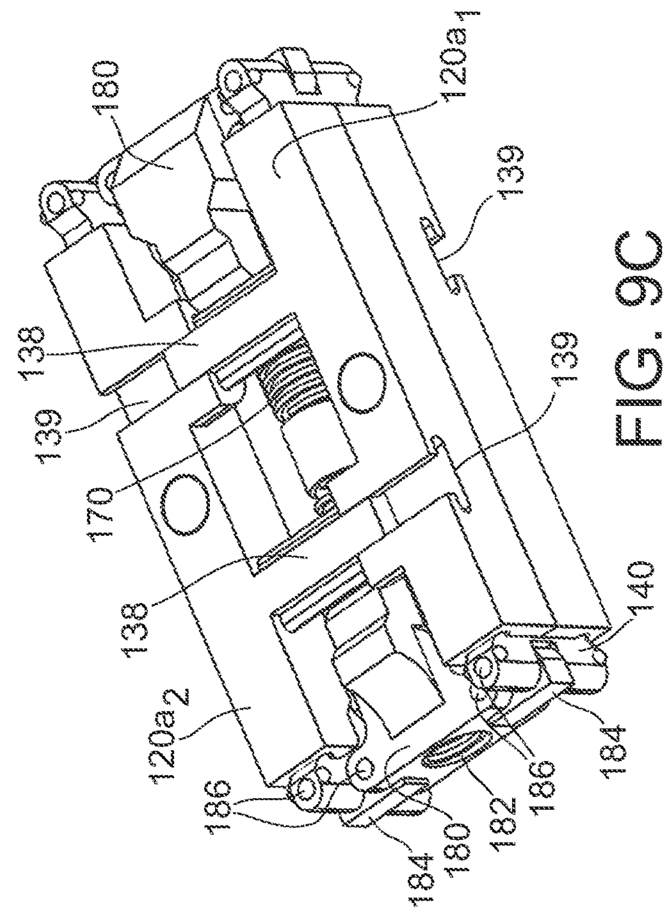

Expansion of the cage 100 will now be explained in reference to FIGS. 9A-9D. As outlined above, and illustrated in annotated FIG. 9A, the cage 100 can be expanded in both the lateral and vertical direction. Lateral and/or vertical expansion can be symmetrical or asymmetrical with respect to opposing bar pairs and/or opposite ends of the same bar pair. FIGS. 9B-9D are perspective views of the example intervertebral cage 100 in transition from an unexpanded configuration (FIG. 9B) to a lateral expanded configuration (FIG. C), to a fully expanded, lateral and vertical, configuration (FIG. 9D). Though not illustrated, asymmetrical expansion can be accomplished by including different height separators 140 between the opposing bar pairs 120$a_1$, 120$b_1$ and 120$a_2$, 120$b_2$. For example, the first bar pair 120$a_1$, 120$b_1$ can include a separator 140 having a first height and the second bar pair 120$a_2$, 120$b_2$ can include a separator 140 having a second/different height. Likewise, asymmetrical expansion can be accomplished by including opposing bar pairs 120$a_1$, 120$b_1$ and 120$a_2$, 120$b_2$ with different height. The example cage 100 includes a threaded rod 170 for controlling/limiting lateral movement between adjacent bar pairs 120$a_1$, 120$b_1$ and 120$a_2$, 120$b_2$. Each of the bars upper and lower bars 120$a$, 120$b$ include an arm 138 for engaging all or a portion of the corresponding recess/channel 139 in the respective opposing bar pair. For example, as illustrated in FIGS. 9A-9D, the first upper bar 120$a_1$ can include a recess 139 for receiving the arm 138 extending from the second upper bar 120$a_2$. Likewise, the second upper bar 120$a_2$ can include a recess 139 for receiving the arm 138 extending from the first upper bar 120$a_1$. Similar arm 138/recess 139 configurations can be included on the first and second lower bar 120$b_1$ and 120$b_2$. Shear movement between the bar pairs 120$a_1$, 120$a_2$ and 120$b_1$, 120$b_2$ can be controlled/limited by contact between the arms 138 and the side walls of the recesses 139. In the example cage 100, the recess 139 can extend through the entire width of the bars 120. Each of the bars 120 can also include a projection 137 extending from the side surface 136 of the bar 120 in a direction towards the opposing upper/lower bar 120$a$, 120$b$. The projection 137 can allow the bar pairs 120$a_1$, 120$a_2$ and 120$b_1$, 120$b_2$ to be in contact once the intervertebral cage 100 is as it maximum horizontal expansion The projection 137 can also contact the threaded rod 170 and/or spacer 180 during lateral expansion. The projection 137 can be used to maintain connection between both sets of bars 120 after the cage 100 is fully laterally expanded, as illustrated in FIGS. 9C and 9D.

As outlined above, the bar pairs 120$a_1$, 120$b_1$ and 120$a_2$, 120$b_2$ are spaced from one another across the vertical midline of the cage 100. The space between the bar pairs 120$a_1$, 120$b_1$ and 120$a_2$, 120$b_2$ can be widened when the cage 100 is expanded in the horizontal/lateral and vertical direction. To cause movement of each bar pair 120$a_1$, 120$b_1$ and 120$a_2$, 120$b_2$ in the lateral and vertical direction the cage 100 includes at least one spacer 180 having a threaded opening 182 for engaging the threaded rod 170. The spacer 180 is coupled to the separator 140 via connectors 184 and pins 186, allowing the spacer 180 to pivot relative to each connector 184 and allowing the connectors 184 to pivot relative to the separator 140.

The spacer 180 is moveable along the threaded rod into and between the space between the bar pairs 120$a_1$, 120$b_1$ and 120$a_2$, 120$b_2$. To cause expansion, the threaded rod 170 engages the threads provided in the threaded opening 182 of the spacer 180 to move the spacer 180 into the space between the bar pairs 120$a_1$, 120$b_1$ and 120$a_2$, 120$b_2$. The spacers 180, for example, may be drawn to each other along the threaded rod 170 by having different direction threads within their respective openings 182. As the spacers 180 advance towards each other, the connectors 184 pivot relative to the spacers 180 and to the separators 140. This movement urges the bars 120 horizontally away from the midline plane of the cage 100 as provided in FIG. 9C, illustrating the cage 100 in a horizontally expanded configuration. Once horizontal expansion is complete, vertical expansion of the cage 100 is accomplished by further engagement between the threaded rod 170 engages the threads provided in the threaded opening 182 of the spacer 180. For example, the connectors 184 can pivot approximately 90° with respect to the spacers 180, further rotation of the threaded rod 170 results in vertical expansion of the cage 100/bars 120. As the spacer 180 advances on the threaded rod 170, the separator 140 is advanced along the contact surface 126 of the bar 120. FIG. 9D illustrates an example cage 100 after both horizontal and vertical expansion.

Figure 10A:
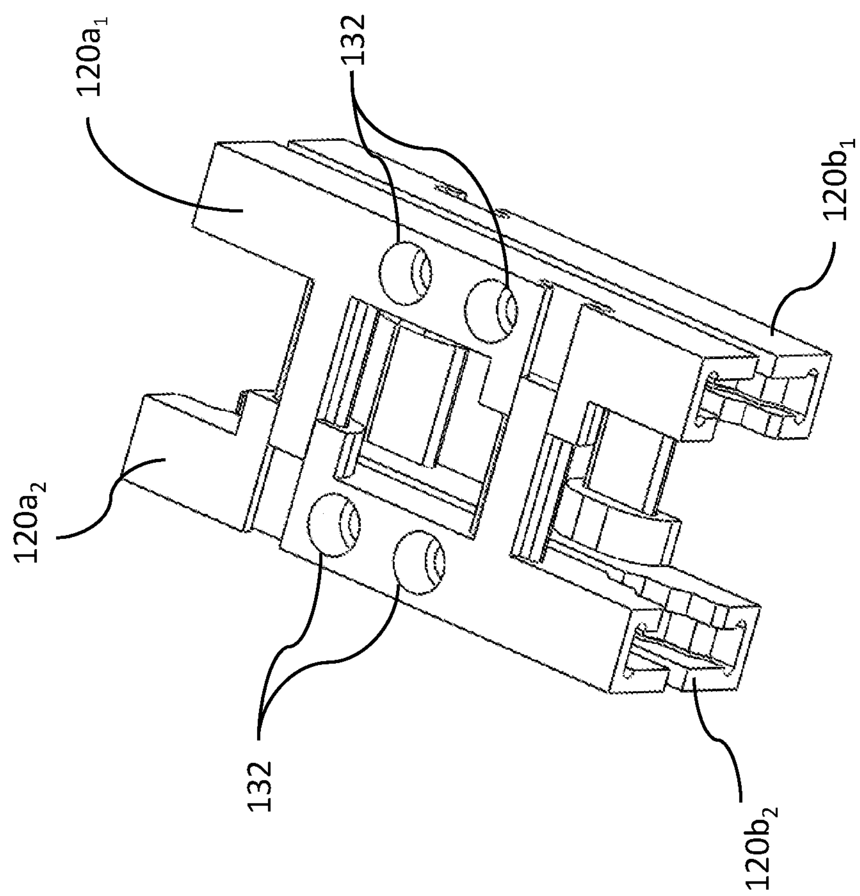
FIG. 10A is a perspective view of example upper and lower bar pairs of an intervertebral cage.
Figure 10B:
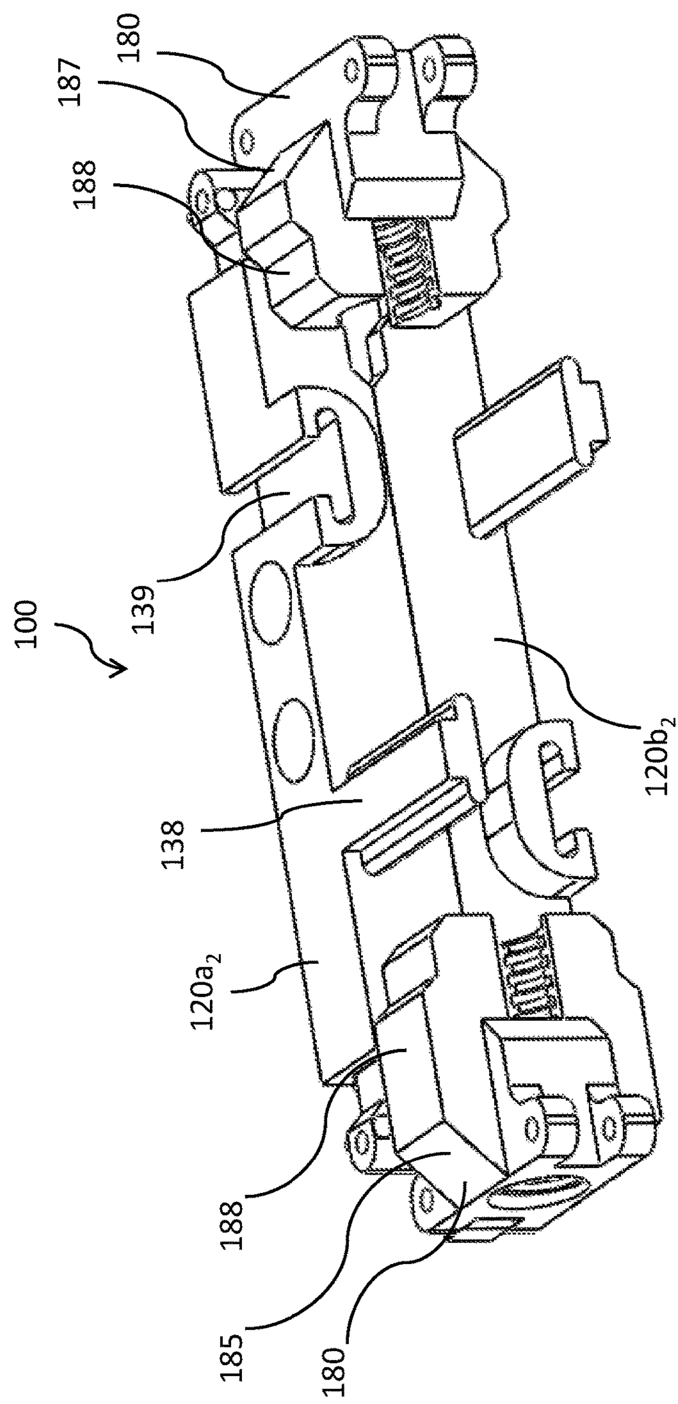
FIG. 10B is a cross-section of the example cage of FIG. 10A in an unexpanded configuration.
Figure 10C:
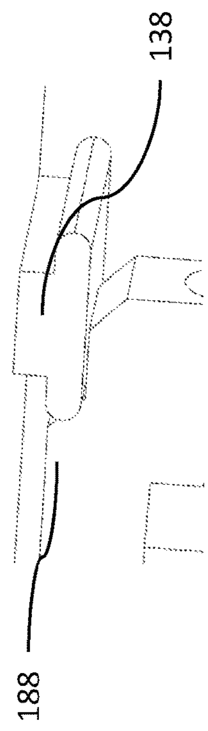
FIG. 10C is a partial cross-section of the example cage of FIG. 10A.
Figure 10D:
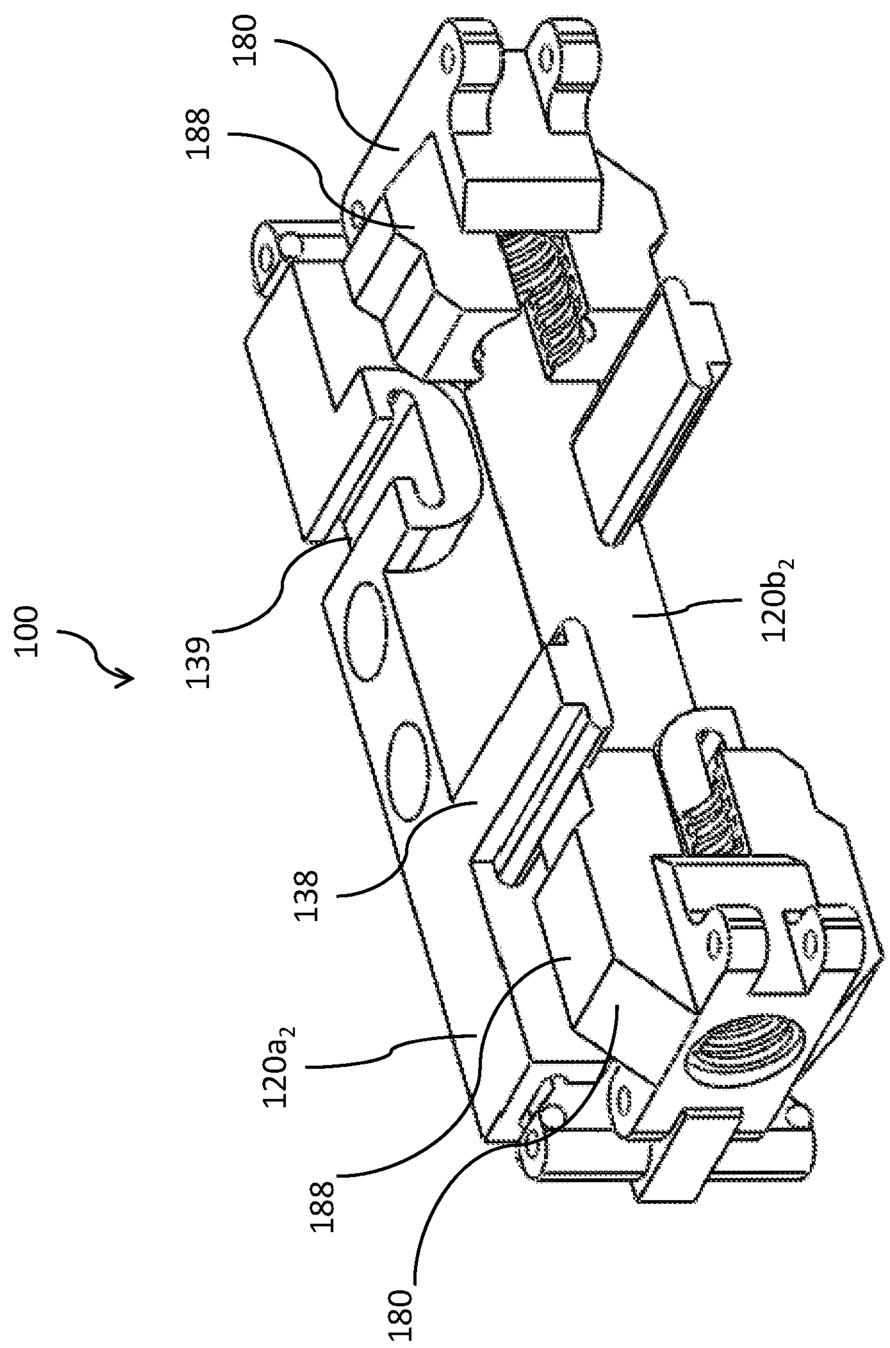
FIG. 10D is a perspective view of an example cage of FIG. 10A in a horizontally expanded configuration.
Figure 10E:
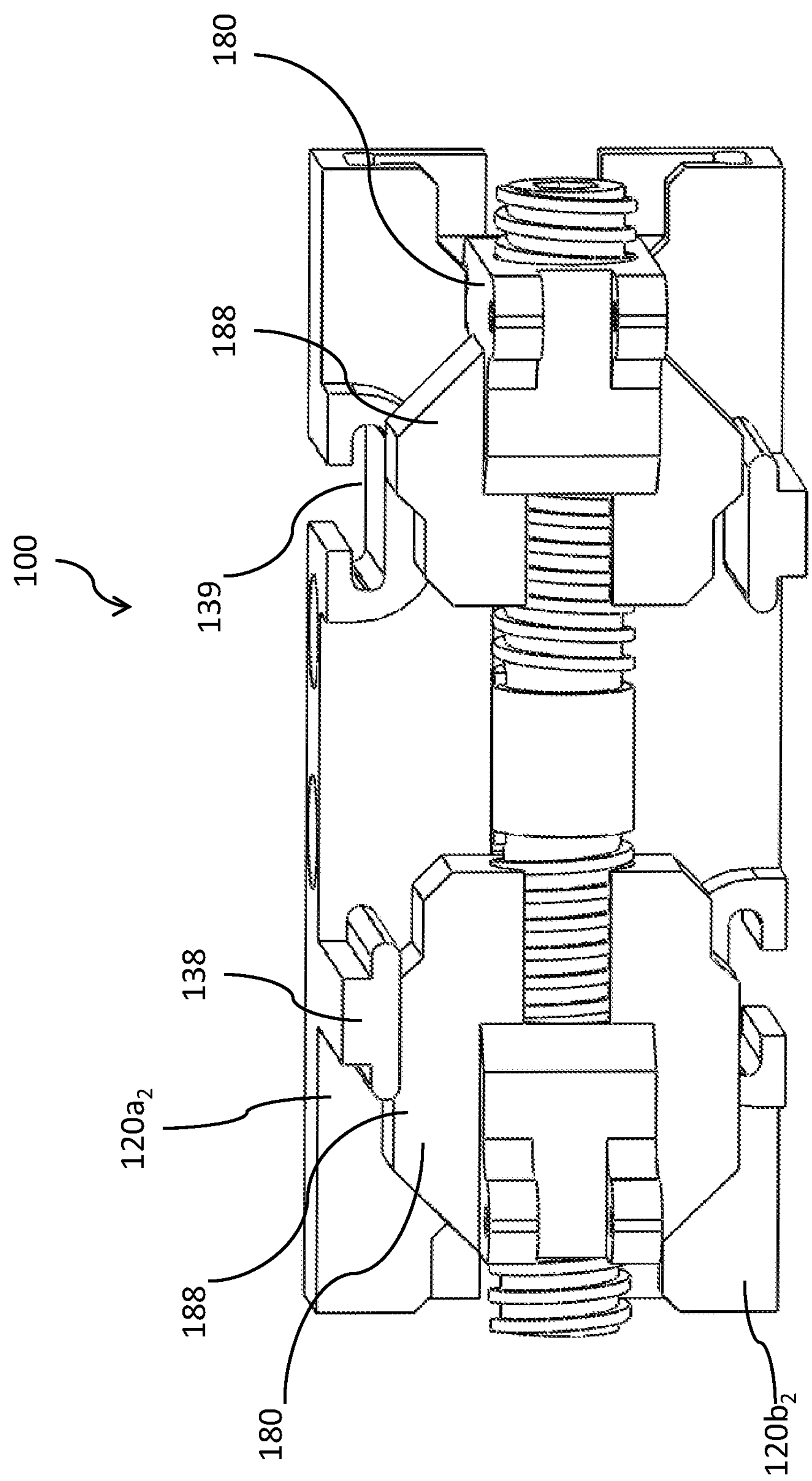
FIG. 10E is a cross-section of the example cage of FIG. 10A in a vertically and horizontally expanded configuration.

FIG. 10A is a perspective view of another example upper and lower bar pair 120$a_1$, 120$b_1$ and 120$a_2$, 120$b_2$ of an intervertebral cage 100. The cage 100 components illustrated in FIGS. 10A-10E includes similar components and function as that described in reference to FIGS. 9A-9D. As provided in FIG. 10A, cage 100 can include two openings 132 for pins 150 on the bars 120. FIGS. 10B-10D are cross-section views of the example cage 100. FIG. 10B provides the cage 100 in an unexpanded configuration. FIG. 10D provides the cage in a fully horizontal expanded configuration. FIG. 10E shows a perspective view of the cage 100 in a horizontally and vertically expanded configuration.

Cage 100 can include spacers 180. The spacers 180 can have varying external structure to facilitate insertion/implantation and/or fusion. For example, the spacer 180 can include a sloped leading surface 185 to facilitate insertion into the vertebral disc space and facilitate vertical expansion of the disc space. The sloped surface 185 can begin proximate the distal end of the spacer 180. Likewise, the spacer 180 located at the trailing end can include a sloped/curved surface 187 starting at position recessed from the leading edge for receiving bone filling material. The curved or sloped surface 187 can receive bone filling material. The curved/sloped surface 187 can also be used to guide bone filling material into the cage 100 when fully expanded.

The spacers 180 can also include a support portion 188 for providing support to the arms 138 extending from the upper and lower bars 120*a*, 120*b*. The support portion 188 can include a lower surface, an incline (that may mirror the incline of the separators 140) and an upper surface. The lower surface provides support to the arms 138 when the cage 100 is in an horizontally expanded configuration (FIG. 10D) and the upper surface provides support to the arms 138 when the cage 100 is in a fully (horizontally and vertically) expanded configuration (FIG. 10E).

Figure 11A:
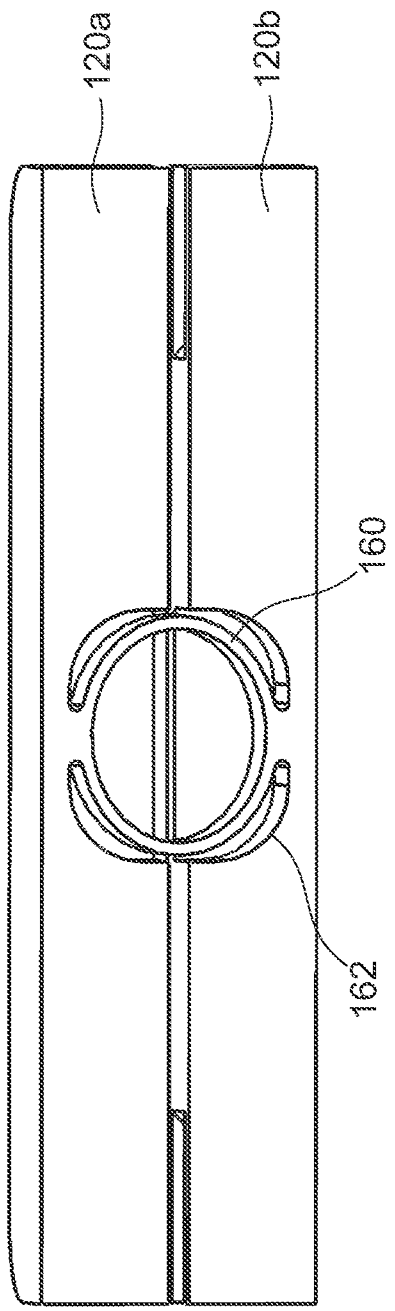
FIG. 11A is a front view of example bar pair connected with a compliant mechanism.
Figure 11B:
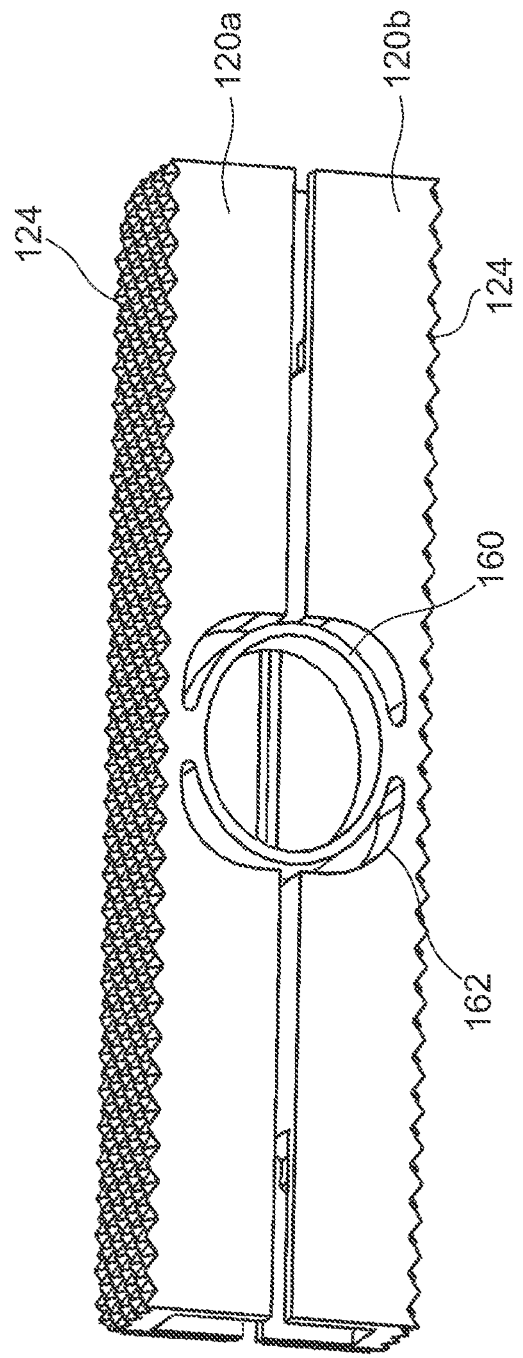
FIG. 11B is a perspective view of the example bar pair connected with a compliant mechanism of FIG. 11A.
Figure 12:
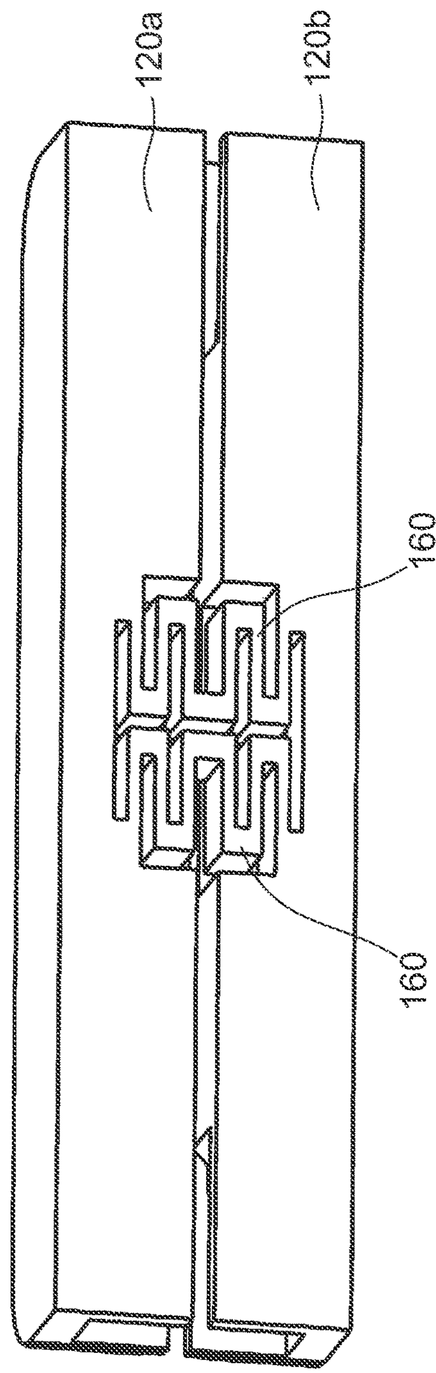
FIG. 12 is a perspective view of an example bar pair connected with a compliant mechanism.
Figure 13:
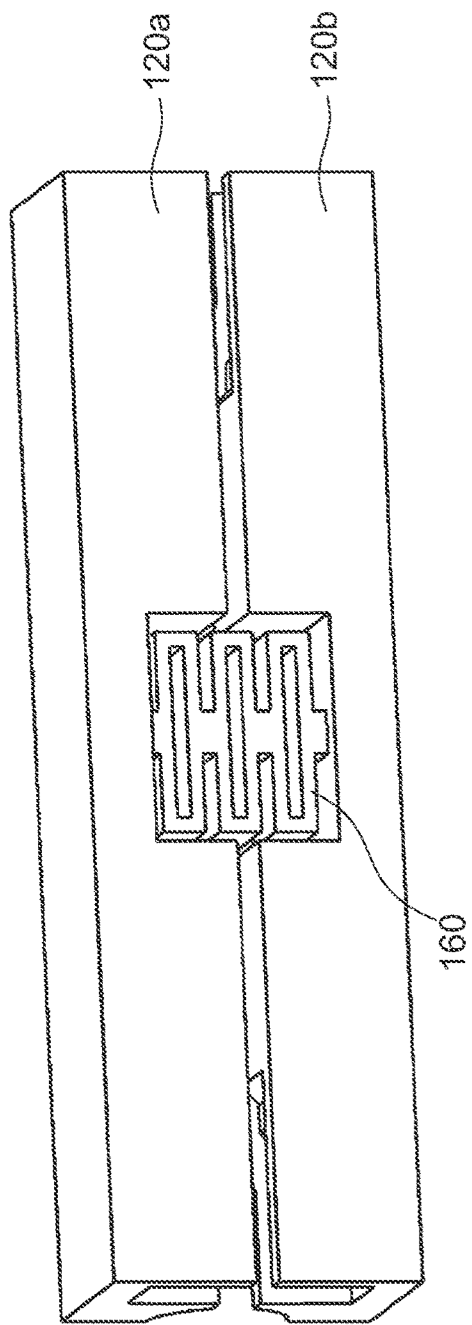
FIG. 13 is a perspective view of an example bar pair connected with a compliant mechanism.
Figure 14:
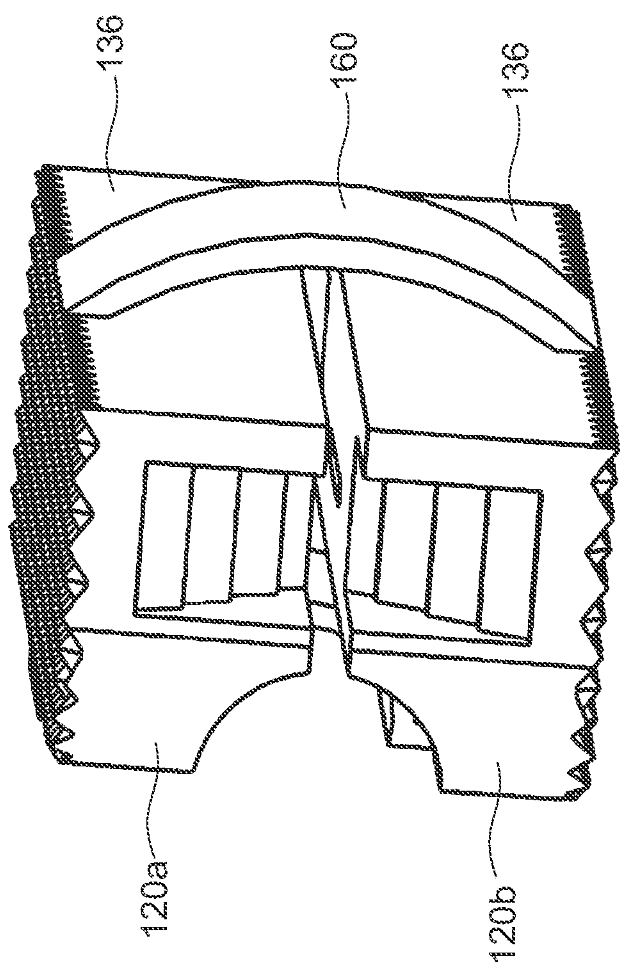
FIG. 14 is a perspective view of an example bar pair connected with a compliant mechanism.

As described above, a separator 140 can be used to define a distance/separation between the upper and lower bar pairs 120*a*, 120*b* and the height of the cage 100. In another example, illustrated in FIGS. 11-15, a compliant mechanism 160 can be used to control expansion and contraction of the upper and lower bars 120*a*, 120*b*. The compliant mechanism 160 can be used in conjunction with or exclusive from the separator 140 and/or pin 150. As the upper and lower bars 120*a*, 120*b* are compressed, the compliant member 160 acts as a spring providing a resistive force. In an example cage 100, the compliant mechanism 160 can be in equilibrium in the fully compressed state and accordingly provides resistive force during distraction of the compliant member 160/upper and lower bars 120*a*, 120*b*. The compliant member 160 can provide a constant resistive force in response to the distraction of the upper and lower bars 120*a*, 120*b*. In another example, the compliant member 160 can provide an irregular or phase resistive force in response to the distraction of the upper and lower bars 120*a*, 120*b*. FIGS. 11A and 11B show a front and perspective view of an example an upper and lower bar pair 120*a*, 120*b* including a round/circular-shaped compliant member 160. The round complaint member 160 can be formed integral to the upper and lower bars 120*a*, 120*b*. Distraction of the upper and lower bars 120*a*, 120*b* causes the compliant member 160 to deform within the opening provided in the bars 120. Distraction can be limited by the clearance provided between the compliant member 160 and the upper and lower bars 120*a*, 120*b*, that is, the distraction can be limited by contact of the compliant member 160 with the surface of the bar opening 162. Distraction can also be limited by modifying the stiffness of the compliant member 160. FIGS. 12 and 13 provide perspective views of an upper and lower bar pair 120*a*, 120*b* including additional examples of compliant members 160. In FIG. 12, the compliant member 160 includes two u-shaped or saddle shaped compliant members 160. In FIG. 13, the compliant member 160 includes a loop-shaped structure. In another example, illustrated in the perspective view of FIG. 14, the compliant member 160 can be coupled to the side surface 136 of the upper and lower bars 120*a*, 120*b*. For example, the compliant member 160 can include an arched structure coupled to the side of the bars and providing resistance against distraction of the upper and lower bars 120*a*, 120*b*.

Figure 15:
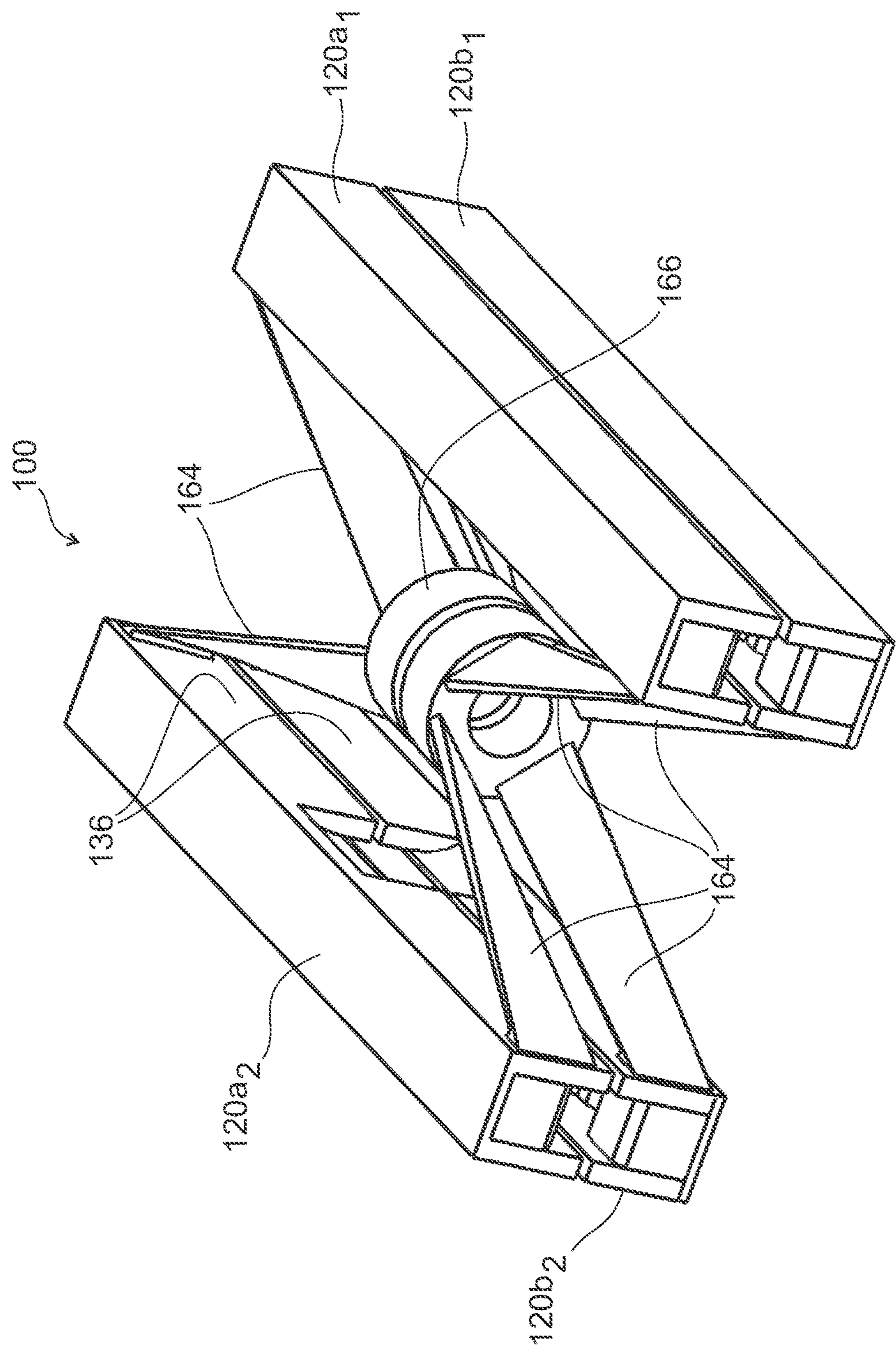
FIG. 15 is a perspective view of an example intervertebral cage connected with compliant mechanisms.
Figure 16B:
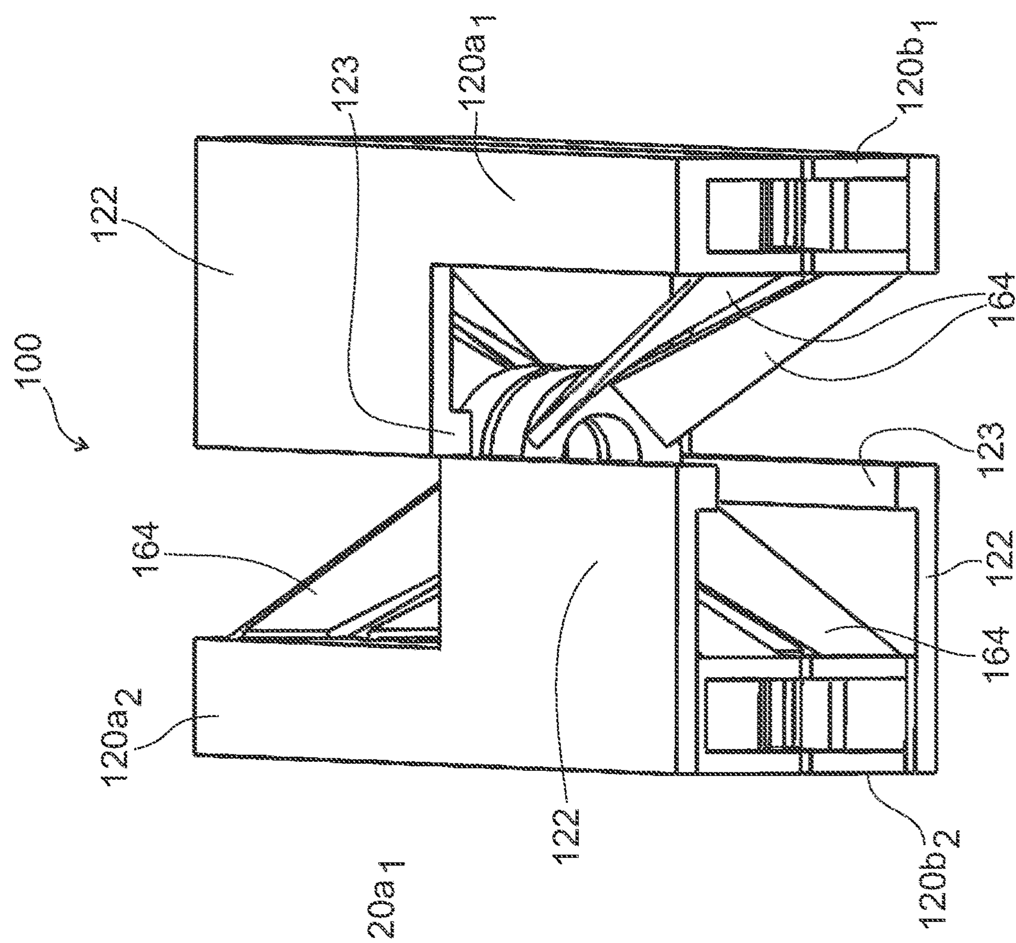
FIGS. 16A and 16B are perspective views of an example intervertebral cage with overhanging supports and compliant mechanisms.
Figure 16A:
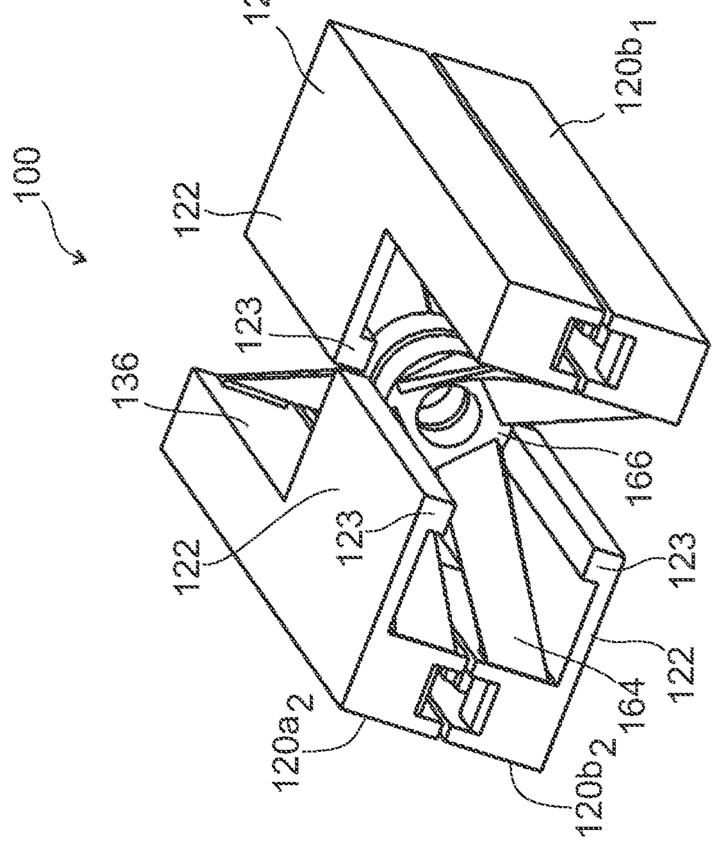

FIGS. 15, 16A and 16B are perspective views of an intervertebral cage 100. The cage 100 includes two upper and lower bar pairs 120$a_1$, 120$b_1$ and 120$a_2$, 120$b_2$, and a compliant member 160. The compliant member 160 can include ligaments/legs 164 extending from a center member 166 and coupled to a side surface 136 of the upper and lower bars 120$a_1$, 120$b_1$ and 120$a_2$, 120$b_2$. The ligaments 164 can provide a resistive force in both the vertical and lateral directions by providing tension between upper and lower bars pairs 120$a_1$, 120$b_1$ and 120$a_2$, 120$b_2$ and the center member. The center member 166 connects the ligaments 164 and can receive a (threaded) bar which can inhibit rotation of the upper and lower bar pairs 120$a_1$, 120$b_1$ and 120$a_2$, 120$b_2$ with respect to the center member 166, thereby limiting shearing (lateral movement) between the upper and lower bar pairs 120$a_1$, 120$b_1$ and 120$a_2$, 120$b_2$. As illustrated in FIGS. 16A and 16B, the upper and lower bars 120$a_1$, 120$b_1$ and 120$a_2$, 120$b_2$ can include an arm 122 extending from the top surface 124 of each of the bars 120. The arm 122 can be used to provide stability to the coupled upper and lower bar pair 120$a_1$, 120$b_1$ and 120$a_2$, 120$b_2$. The arms 122 can be used maintain the bar pairs in a parallel configuration. For example, the arms 122 can include a bottom projection/lip 123 that engages the center member 166 of the compliant mechanism 160. This engagement can be used to maintain a parallel relationship between the bar pairs 120$a_1$, 120$b_1$ and 120$a_2$, 120$b_2$ and further limit rotational movement of the cage 100. The arms 122 can be constructed from a rigid, semi-rigid or compliant material. In one example, the arms 120 can bend or deform to accommodate the endplate of the adjacent vertebral body.

Figure 17A:
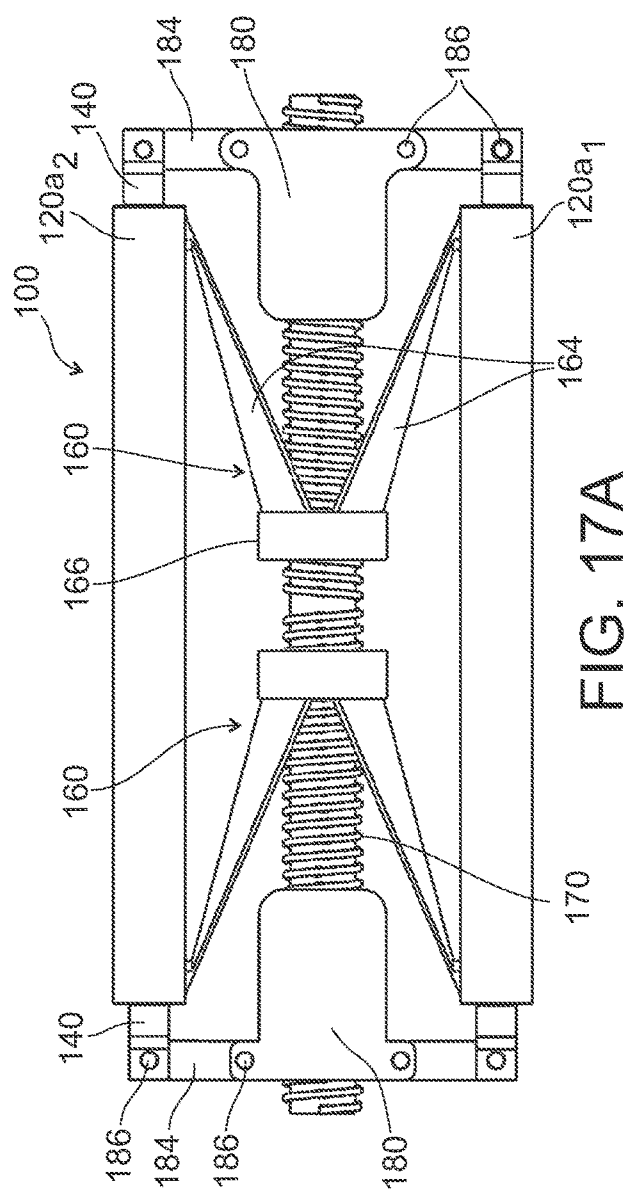
FIG. 17A is a top view of an example intervertebral cage with compliant mechanisms in a horizontally expanded configuration.
Figure 17B:
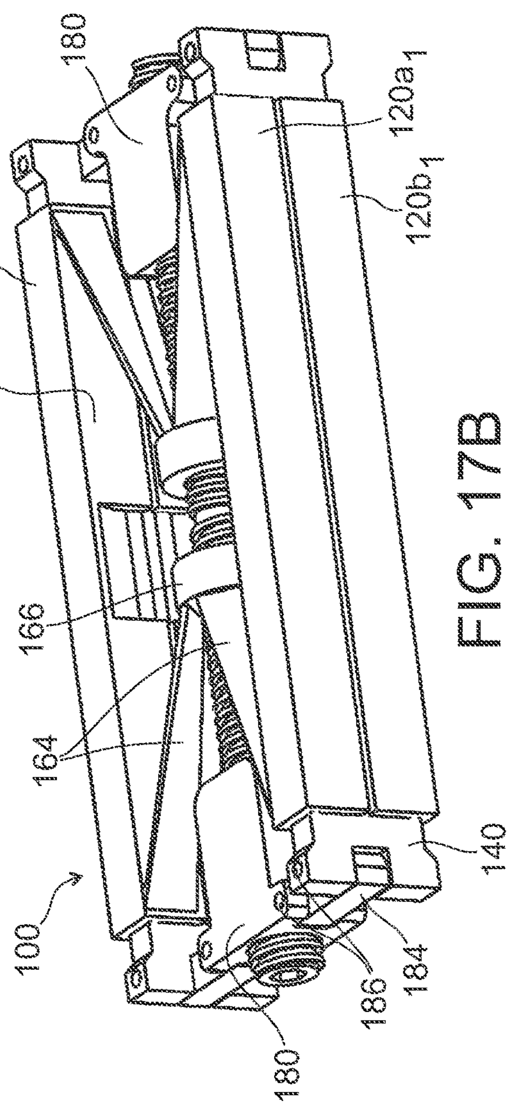
FIGS. 17B and 17C are perspective views of the example intervertebral cage with compliant mechanisms of FIG. 17A.
Figure 17C:
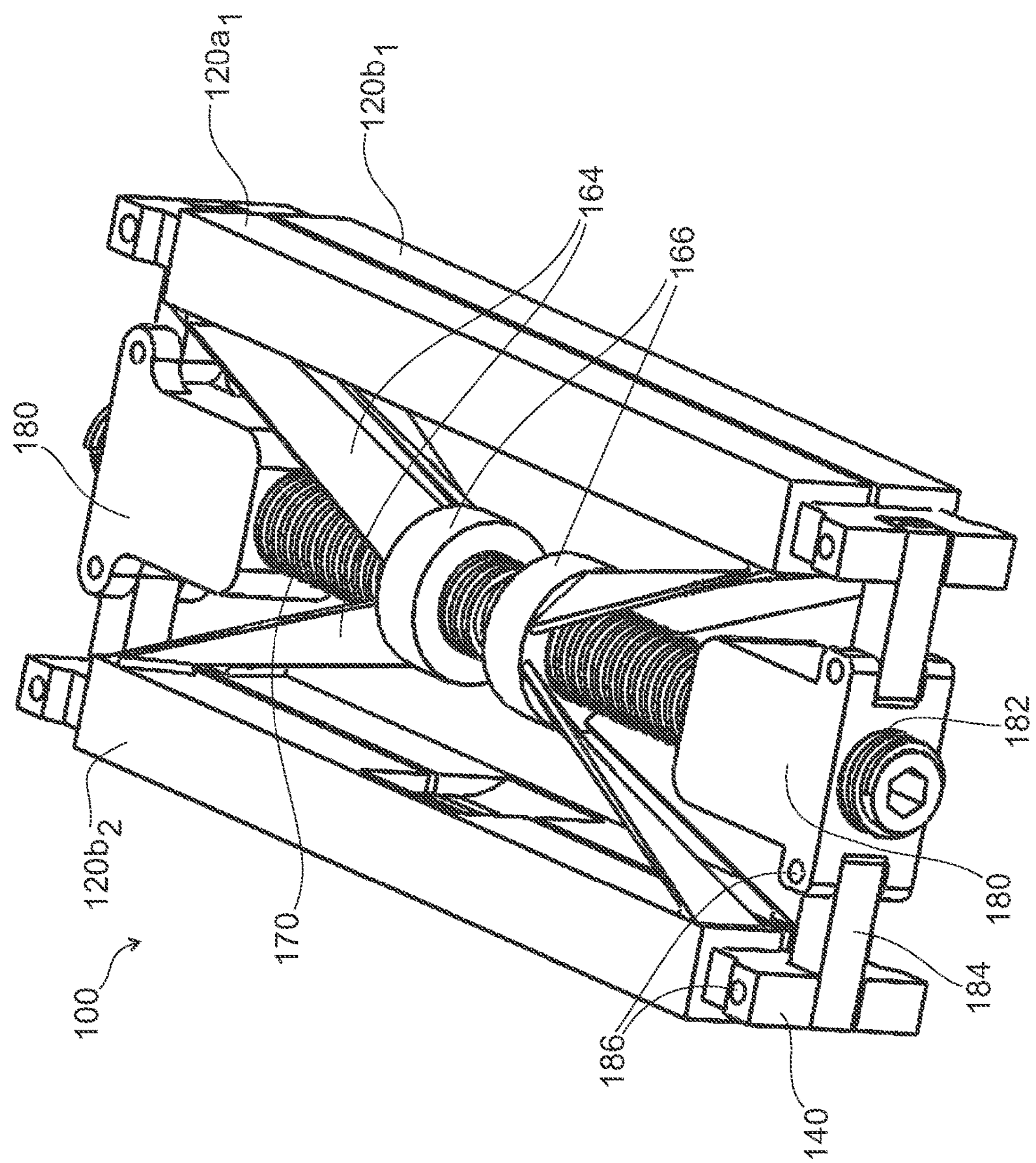

FIGS. 17A-17C provide another example intervertebral cage 100 including a threaded rod 170 and a compliant member 160 for controlling/limiting lateral movement between adjacent bar pairs. The example cage 100 can include two upper and lower bar pairs (each pair including an upper bar and a lower bar) 120$a_1$, 120$b_1$ and 120$a_2$, 120$b_2$, a threaded rod 170 extending between the bar pairs along the midline of the cage 100, spacers 180 operatively coupled to the threaded rod 170 and the bar pairs 120$a_1$, 120$b_1$ and 120$a_2$, 120$b_2$ via connectors 184. The example cage 100 can also include two compliant members 160 having ligaments/legs 164 extending from a center member 166 and coupled to a side surface 136 of the upper and lower bars 120*a*, 120*b*. The ligaments 164 can provide a resistive force in both the vertical and lateral directions by providing tension between upper and lower bars pairs 120$a_1$, 120$b_1$ and 120$a_2$, 120$b_2$ and the center members 166. The center member 166 connects the ligaments 164 and can receive a partial or fully threaded bar 182 which can inhibit rotation of the upper and lower bar pairs 120$a_1$, 120$b_1$ and 120$a_2$, 120$b_2$ with respect to the center members 166 and each other, thereby limiting shearing (lateral movement) between the upper and lower bar pairs 120$a_1$, 120$b_1$ and 120$a_2$, 120$b_2$. The bar pairs 120$a_1$, 120$b_1$ and 120$a_2$, 120$b_2$ are spaced from one another across the vertical midline of the cage 100. The space between the bar pairs 120$a_1$, 120$b_1$ and 120$a_2$, 120$b_2$ can be widened when the cage 100 is expanded in the horizontal and vertical direction by rotation of the threaded shaft 170 and engagement of the spacers 180 and separators 140, as outlined above.

FIGS. 18A-18K provide another example cage 200. Similar to cage 100 described above, cage 200 is designed for implantation and fusion between adjacent vertebrae. It is contemplated that cage 100 and cage 200 may include like components. Where possible, corresponding element numbers are used to describe like components.

As will be described in more detail below, cage 200 can expand horizontally and/or vertically. For example, once positioned the cage 200 can be expanded in a horizontal direction in the plane of the intervertebral space in which the cage 200 is located. The cage 200 can also be expanded in a vertical direction to increase the vertical separation between the adjacent vertebrae. A single actuator, or plurality of actuating devices, can be used to provide horizontal and vertical expansion.

The cage 200 can include a pair of front and back lateral bars 210*a*, 210*b* and a pair of upper and lower horizontal bars 220*a*, 220*b*. The lateral and horizontal bars surround a central component 240. The cage 200 can include a plurality of actuating members, for example, threaded rod 270 and screws 275. The threaded rod 270 and screws 275 can be used to drive the expandable surfaces (lateral and horizontal bars 210, 220) of the cage 200.

Figure 18A:
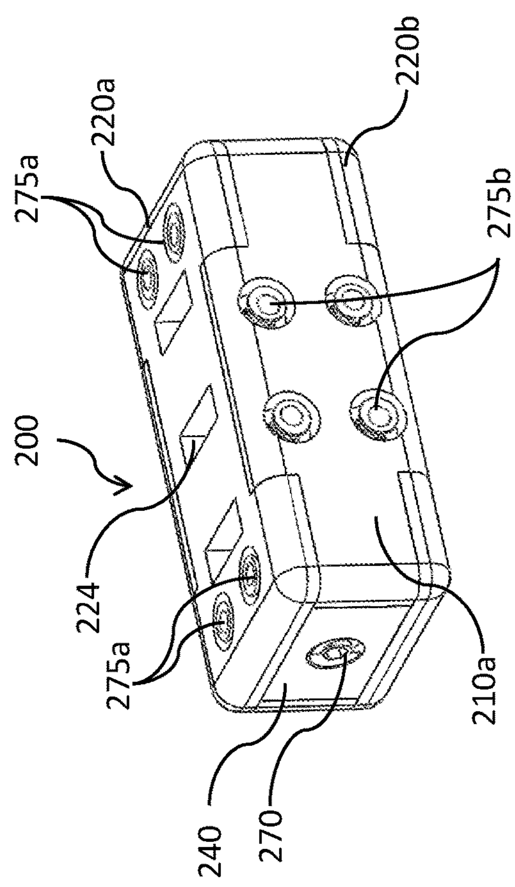
FIGS. 18A-18C are perspective views of an example intervertebral cage.
Figure 18C:
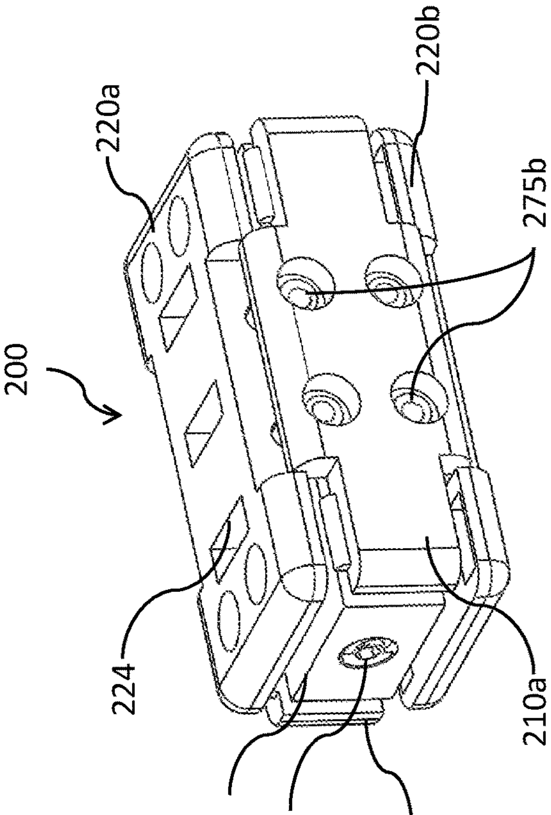
Figure 18B:
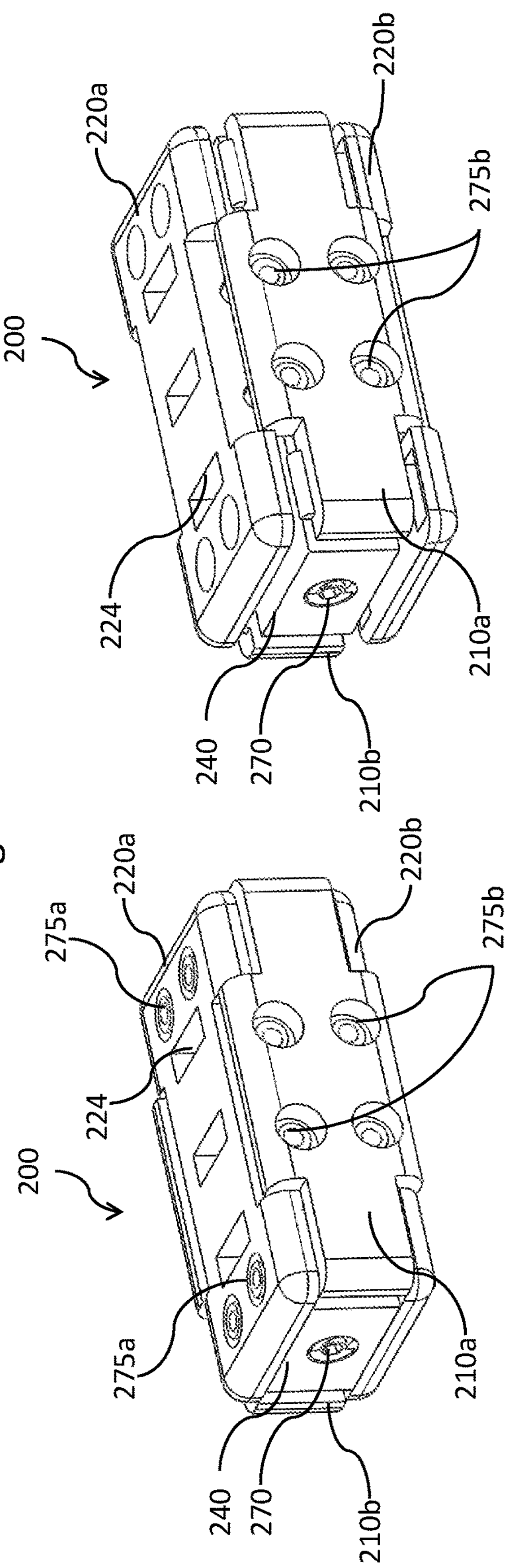

As will be described in more detail below, the lateral and vertical space between the lateral and horizontal bars 210, 220 can be increased/decreased as the cage 200 is expanded/retracted. FIG. 18A is a perspective view of the cage 200 in an unexpanded configuration. FIG. 18B is a perspective view of the cage 200 in a horizontally expanded configuration. FIG. 18C is a perspective view of the cage 200 in a fully expanded (horizontal and vertical) configuration.

Figure 18D:
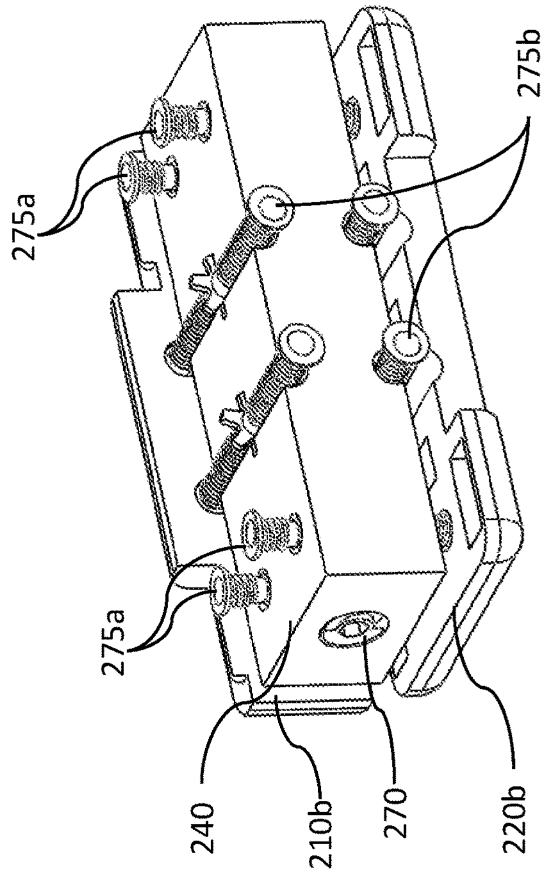
FIG. 18D is a perspective view of a lateral and a horizontal bar, central component, and actuating members.
Figure 18E:
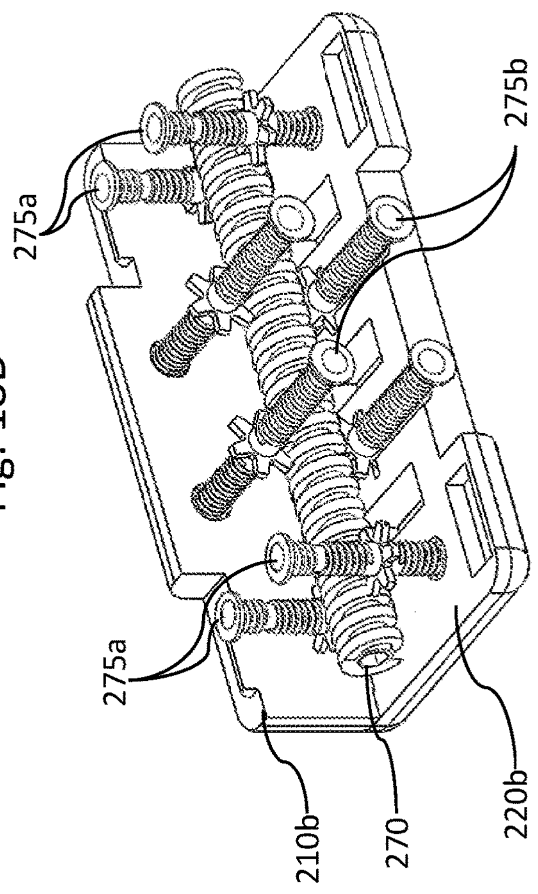
FIG. 18E is a perspective view of a lateral and a horizontal bar and actuating members.
Figure 18F:
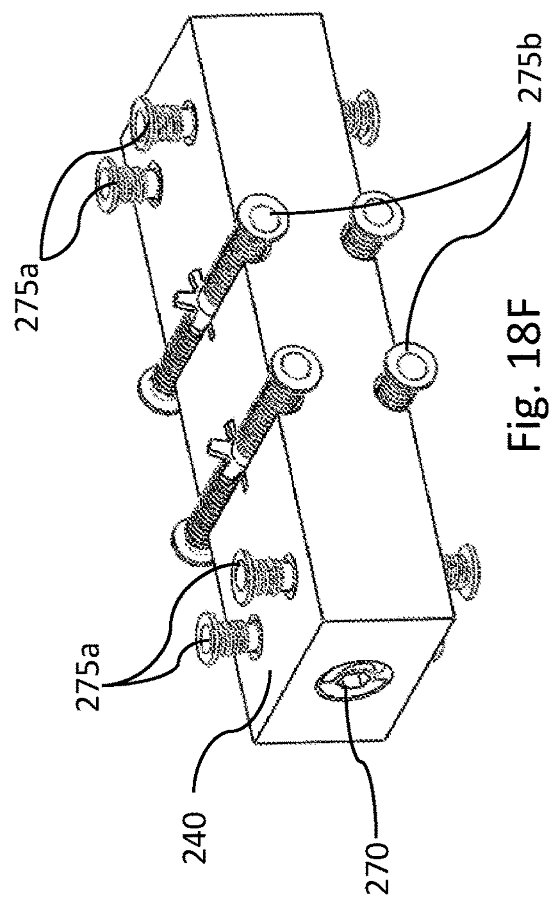
FIG. 18F is a perspective view of a central component and actuating members.
Figure 18G:
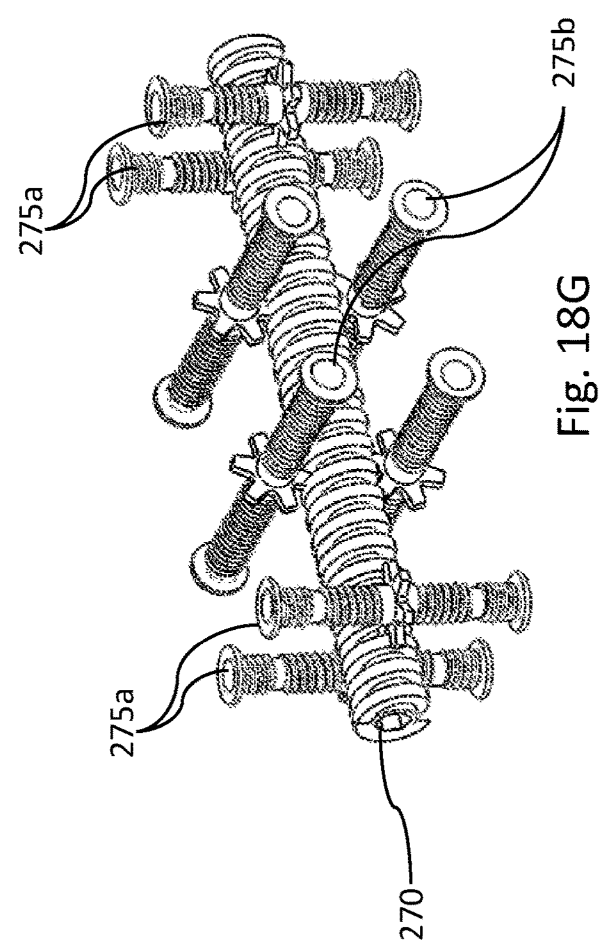
FIG. 18G is a perspective view of the actuating members.
Figure 18H:
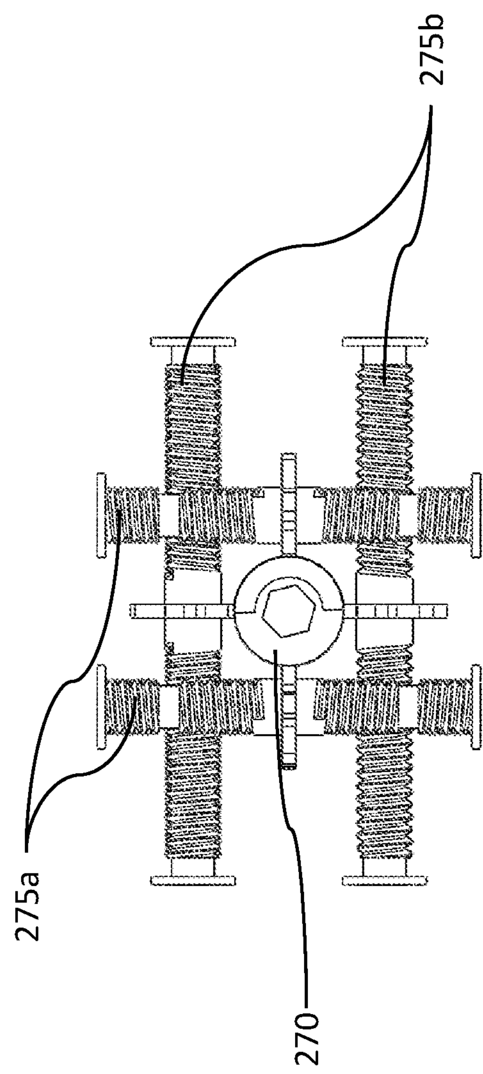
FIG. 18H is an end view of the actuating members.

FIGS. 18D-18G provide perspective views of various cage 200 components. As illustrated, the threaded rod 270 can extend through a bore provided in the central component 240. The bore can include a threaded or non-threaded interior surface. The screws 275 can extend through bores and/or channels provided in the central component 240. For example, as illustrated in FIG. 18D, vertical screws 275*a* can extend through bores extending between the top and bottom surface of the central component 240. Likewise, horizontal screws 275*b* can extend through horizontal channels/openings extending between the front and back side surfaces of the central component 240. The central component 240 can have braces extending from the horizontal/lateral surface to maintain the distance between the screws 275 and the central component 240. As provided in FIGS. 18E, 18G and 18H, screws 275 can movably engage the threaded rod 270 in an orthogonal arrangement. For example, screws 275 and threaded rod 270 can form a worm drive. In an example cage 200, the threads of the threaded rod 270 engage corresponding gears and/or threads of the screws 275. Each of the vertical screws 275*a* and horizontal screws 275*b* can engage and rotate with the threaded rod 270.

As illustrated in FIGS. 18A-18E, the screws 275 extend through the central component 240 and engage the lateral and horizontal bars 210, 220. For example, the vertical screws 275*a* engage the top and bottom horizontal bars 220*a*, 220*b*. Likewise, the horizontal screws 275*b* engage the front and back lateral bars 210*a*, 210*b*. The screws 275 can engage the lateral and horizontal bars 210, 220 via a threaded connection provided in the corresponding lateral or horizontal bar 210, 220. Rotation of the screws 275 can result in translation of the corresponding lateral or horizontal bar 210, 220. Screws 275 can include a head/lip for limiting motion between corresponding lateral or horizontal bar 210, 220. As provided in FIGS. 18A and 18B, the bores provided in the lateral and horizontal bars 210, 220 can include a counter bore/recess sized to accommodate the head/lip of the screw 275.

Figure 18I:
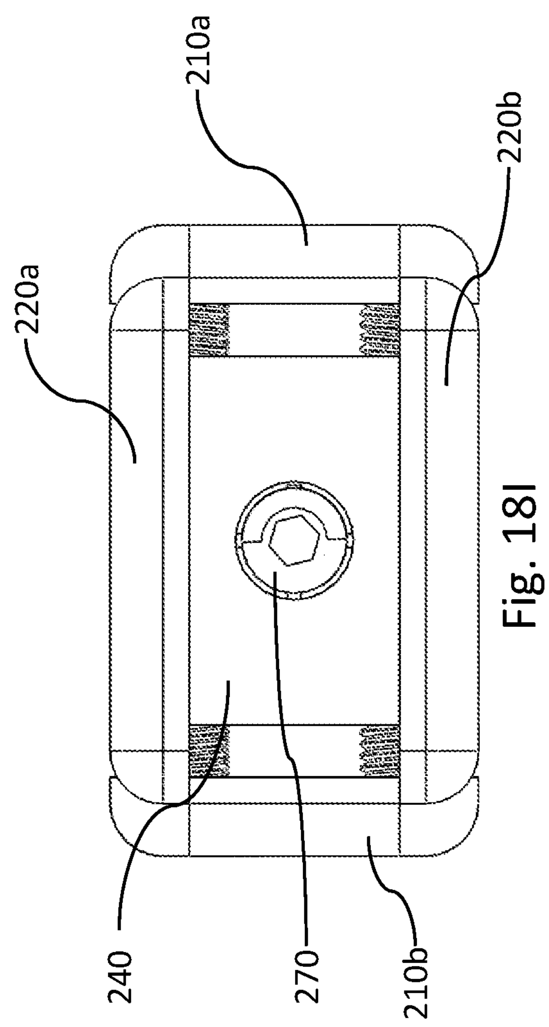
FIG. 18I is an end view of the example cage of FIG. 18A in horizontally expanded configuration.
Figure 18J:
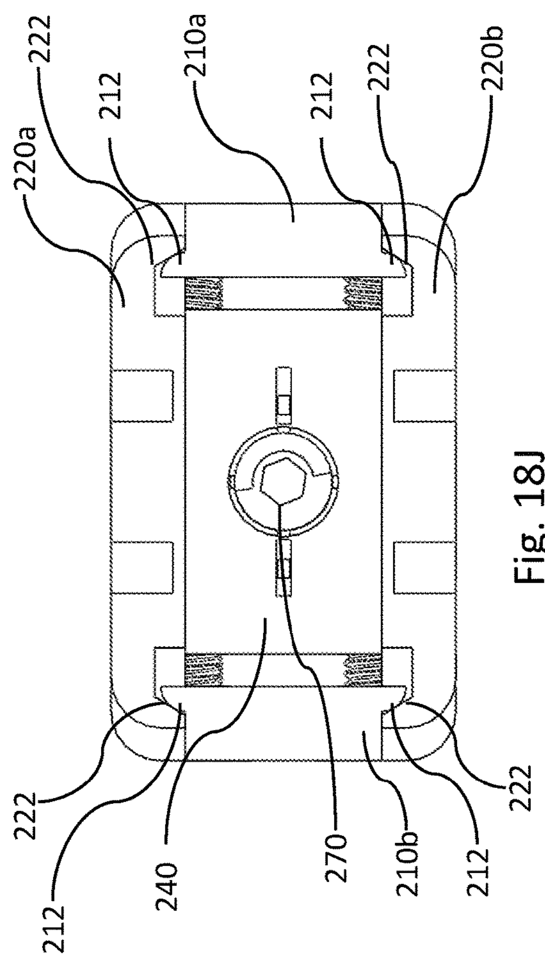
FIG. 18J is a sectional view of the example cage of FIG. 18A in a horizontally expanded configuration.

The cage 200 can be expanded horizontally and/or vertically. As outlined above, it is contemplated that the cage 200 is expanded horizontally, followed by vertical expansion. FIGS. 18B and 18I illustrate cage 200 in horizontally expanded configuration. To ensure that horizontal expansion occurs before vertical expansion, the top and bottom horizontal bars 220*a*, 220*b* do not contact the threaded portions of the vertical screws 275*a*. Accordingly, vertical expansion of the cage 200 will not occur until contact between the vertical screws 275*a* and the top and bottom horizontal bars 220*a*, 220*b*. FIG. 18J illustrates the cage 200 in an almost complete horizontally expanded configuration. As provided in FIG. 18J, the inside surface of the lateral bars 210 can include a lip/protrusion 212 for engaging a corresponding beveled edge 222 included on an inside surface of the horizontal bars 220. Engagement between the lip 212 and edge 222 can cause articulation between the lateral bars 210 and horizontal bars 220. That is, engagement between the lip 212 and edge 222 directs the upper and lower horizontal bars 220*a*, 220*b* vertically, thereby causing the upper and lower horizontal bars 220*a*, 220*b* to engage the vertical screws 275*a*.

Figure 18K:
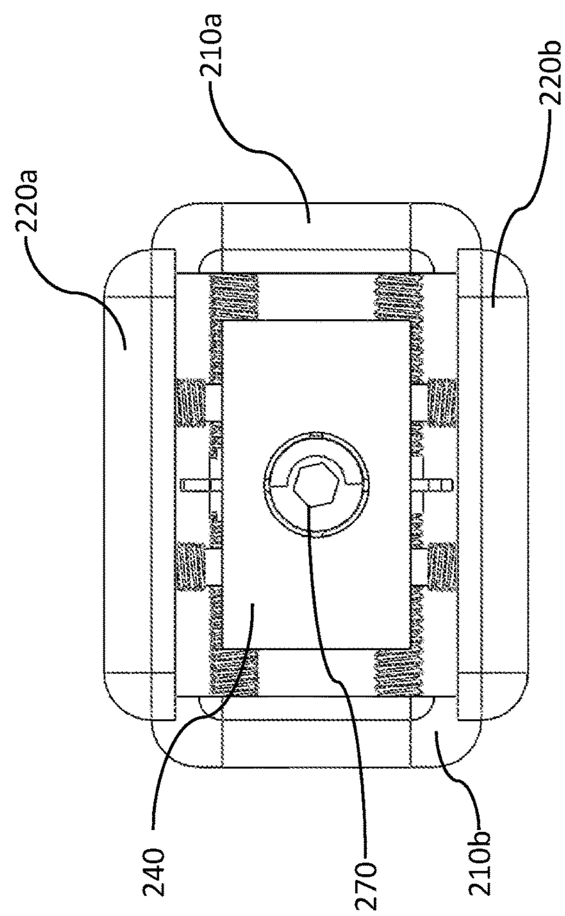
FIG. 18K is an end view of the example cage of FIG. 18A in a vertically and horizontally expanded configuration.

Once the horizontal expansion of the front and back lateral bars 201*a*, 210*b* is complete, the vertical screws 275*a* engage the upper and lower horizontal bars 220*a*, 220*b*. Additional rotation of the threaded rod 270 results in vertical expansion/separation of the upper and lower horizontal bars 220*a*, 220*b*. To inhibit excess lateral expansion, while vertical expansion is occurring, the ends of horizontal screws 275*b* do not include threads. Accordingly, only vertical expansion occurs at the end phase of the cage 200 expansion. FIG. 18K illustrates the cage 200 in a vertically and horizontally expanded configuration.

The cage 200 can include surface features, treatment and/or recesses to encourage fusion between the cage 200 and the adjacent vertebral bodies. As illustrated in FIGS. 18A-18C, the lateral bars 210 and/or horizontal bars 220 can include rectangular openings 224 to receive bone filing material/biologics. The openings 224 can also permit the worm/gears associated with the screws 275 to rotate without impacting or otherwise damaging the lateral and/or horizontal bars 210, 220.

One or more components of the cage 100/200 may be made from any biocompatible material known including, for example, metals such as titanium, titanium alloys, stainless steel and cobalt chromium. Other materials include, for example, composites, polymers, ceramics, bone (allograft) and any other materials suitable for the cage 100/200. In one example, the cage 100/200 can be constructed from a radiopaque material including, for example, stainless steel such as 17-4PH stainless steel. Likewise, one or more components of the cage 100/200 can be constructed from a radiolucent material to enhance visibility of the assembly during radiographic imaging Example radiolucent materials can include “life science” grade PEEK (Ketron 450G PEEK). Life science grade PEEK can improve wear and abrasion characteristics as well as provide high yield strength.

While the foregoing description and drawings represent the an example implementation of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the example implementations described above without departing from the broad inventive concept thereof. It is understood, therefore, that this invention is not limited to the particular examples disclosed, but it is intended to cover modifications within the spirit and scope of the present invention, as defined by the following claims.

What is claimed is:

1. An intervertebral cage comprising:
- a first bar pair on a first lateral side, the first bar pair comprising a first upper bar and an opposing first lower bar;
- a first pin extending between the first upper bar and the first lower bar; and
- a first separator movable between the first upper bar and the first lower bar to direct vertical movement therebetween;
- a second bar pair on a second lateral side, the second bar pair comprising a second upper bar and an opposing second lower bar;
- a spacer movable into a space between the first and second bar pairs; and
- a coupling between the first separator and the spacer, wherein the coupling comprises at least one pin allowing for pivotable movement between the first separator and the spacer.

2. The intervertebral cage of claim 1, further comprising a second pin extending between the second upper bar and the second lower bar, and a second separator movable between the second upper bar and the second lower bar to direct vertical movement therebetween.

3. The intervertebral cage of claim 1, further comprising a drive mechanism for directing lateral expansion of the first bar pair and the second bar pair.

4. The intervertebral cage of claim 3, wherein the drive mechanism further directs vertical movement between the first upper and lower bars of the first bar pair via the first separator.

5. The intervertebral cage of claim 3, wherein the first separator is coupled to the drive mechanism via the spacer, and wherein activation of the drive mechanism moves the spacer along a longitudinal axis of the drive mechanism and towards a midline of the intervertebral cage during lateral expansion of the first and second bar pairs.

6. The intervertebral cage of claim 5, wherein the spacer includes a threaded opening for engaging a threaded rod of the drive mechanism.

7. The intervertebral cage of claim 1, wherein the spacer is movable into the space between the first and second bar pairs during lateral expansion of the first and second bar pairs.

8. The intervertebral cage of claim 7, wherein the spacer includes a sloped leading surface to facilitate insertion into a vertebral disc space.

9. The intervertebral cage of claim 1, wherein at least one of the first upper bar and the first lower bar include an inclined separator contact surface, wherein the first separator includes an inclined bar contact surface for contacting the corresponding inclined separator contact surface, such that the first separator is movable along the separator contact surface.

10. The intervertebral cage of claim 9, wherein the separator is moveable along the separator contact surface to cause movement of the upper and lower bars towards and away from each other.

11. The intervertebral cage of claim 1, wherein movement of the first separator between the first upper and first lower bars causes vertical separation of the bars in a direction substantially parallel to a longitudinal plane of the cage.

12. The intervertebral cage of claim 1, wherein at least one of the first upper bar and the first lower bar include a groove on an inside surface of the bar, wherein the separator includes a projection extending from a side surface of the separator, the projection sized and configured to engage the groove of the at least one first upper and lower bars.

13. The intervertebral cage of claim 12, wherein the groove is inclined.

14. The intervertebral cage of claim 1, wherein the first pin includes a head received within a recess included in at least one of the first upper and lower bars.

15. The intervertebral cage of claim 1, wherein the first upper and lower bars include teeth extending from upper and lower contact surfaces of the first upper and lower bars, respectively, for providing engagement between the first upper and lower bars and adjacent vertebral bodies.

16. An intervertebral cage, comprising:
- a first bar pair including a first upper bar and an opposing first lower bar;
- a first separator movable between the first upper bar and the first lower bar to move apart the first upper bar and the first lower bar;
- a second bar pair including a second upper bar and an opposing second lower bar;
- a spacer movable into a space between the first and second bar pairs; and
- a coupler coupled to the first separator and the spacer, wherein the coupler comprises at least one pin configured to allow rotational movement between the first separator and the spacer.

17. The intervertebral cage of claim 16, further comprising a drive mechanism for directing lateral expansion of the first and second bar pairs.

18. The intervertebral cage of claim 17, wherein the drive mechanism further directs vertical movement between the first upper and lower bars of the first bar pair via the first separator.

19. The intervertebral cage of claim 16, wherein the spacer is movable into the space between the first and second bar pairs during lateral expansion of the first and second bar pairs.

20. An intervertebral cage, comprising:
- a first bar pair including a first upper bar and an opposing first lower bar;

a first pin extending between the first upper bar and the first lower bar; and a first separator movable between the first upper bar and the first lower bar to vertically expand the first bar pair;

a second bar pair including a second upper bar and an opposing second lower bar;

a spacer movable to be positioned directly between the first bar pair and the second bar pair to laterally expand the first and second bar pairs; and a coupler between the first separator and the spacer, wherein the coupler comprises at least one pin pivotably coupling movement of the first separator to the spacer.

21. The intervertebral cage of claim 20, wherein the spacer includes a sloped leading surface to facilitate insertion into a vertebral disc space.

22. The intervertebral cage of claim 20, wherein at least one of the first upper bar and the first lower bar include an inclined separator contact surface, wherein the first separator includes an inclined bar contact surface for contacting the corresponding inclined separator contact surface, such that the first separator is movable along the separator contact surface.

23. The intervertebral cage of claim 20, wherein movement of the first separator between the first upper and first lower bars causes vertical separation of the bars in a direction substantially parallel to a longitudinal plane of the cage.

24. The intervertebral cage of claim 20, wherein the coupler further comprises a connector, and wherein the at least one pin includes:

a first pin rotatably coupling the connector to the first separator; and a second pin rotatably coupling the connector to the spacer.

* * * * *